(12) United States Patent
Yodfat et al.

(10) Patent No.: US 8,715,232 B2
(45) Date of Patent: May 6, 2014

(54) PORTABLE INFUSION PUMP WITH CANNULA INSERTER AND PAIN REDUCTION MECHANISM

(75) Inventors: Ofer Yodfat, Maccabim-Reut (IL); Illai Gescheit, Tel Aviv (IL)

(73) Assignee: Roche Diagnostics Operations Inc., Indianapolis, IN (US)

( * ) Notice: Subject to any disclaimer, the term of this patent is extended or adjusted under 35 U.S.C. 154(b) by 89 days.

(21) Appl. No.: 12/452,187

(22) PCT Filed: Jun. 25, 2008

(86) PCT No.: PCT/IL2008/000861
§ 371 (c)(1),
(2), (4) Date: Dec. 18, 2009

(87) PCT Pub. No.: WO2009/001347
PCT Pub. Date: Dec. 31, 2008

(65) Prior Publication Data
US 2010/0106088 A1    Apr. 29, 2010

Related U.S. Application Data

(60) Provisional application No. 60/937,163, filed on Jun. 25, 2007, provisional application No. 60/937,155, filed on Jun. 25, 2007, provisional application No. 60/937,214, filed on Jun. 25, 2007.

(51) Int. Cl.
*A61M 5/00* (2006.01)
*A61M 5/178* (2006.01)

(52) U.S. Cl.
USPC .................. 604/112; 604/164.01; 604/164.12

(58) Field of Classification Search
USPC .................................. 604/112, 113, 114, 115
See application file for complete search history.

(56) References Cited

U.S. PATENT DOCUMENTS

| | | |
|---|---|---|
| 2,746,264 A | 5/1956 | Keyes |
| 2,982,112 A | 5/1961 | Keyes |
| 3,327,713 A | 6/1967 | Eidus |
| 3,826,264 A | 7/1974 | Gunther |
| 4,614,191 A | 9/1986 | Perier |
| 4,646,735 A | 3/1987 | Seney |

(Continued)

FOREIGN PATENT DOCUMENTS

| | | |
|---|---|---|
| DE | 199 32 352 | 1/2001 |
| DE | 10 2004 025651 | 12/2005 |

(Continued)

OTHER PUBLICATIONS

Routasalo et al, "The Right to Touch and Be Touched", *Nursing Ethics* 3(2): 165-176 (1996).

(Continued)

*Primary Examiner* — Laura Bouchelle
*Assistant Examiner* — Weng Lee
(74) *Attorney, Agent, or Firm* — Mintz, Levin, Cohn, Ferris, Glovsky and Popeo, P.C.

(57) ABSTRACT

An apparatus for insertion of a subcutaneously insertable element within a body of a patient is described: The apparatus is used for delivery of a therapeutic fluid into a body of a patient and/or sensing of a bodily analyte The apparatus allows alleviating of pain associated with the penetrating of the skin of the patient during needle insertion.

29 Claims, 29 Drawing Sheets

(56) References Cited

U.S. PATENT DOCUMENTS

| | | | |
|---|---|---|---|
| 4,725,265 A * | 2/1988 | Sairenji | 604/112 |
| 4,755,173 A | 7/1988 | Konopka et al. | |
| 5,176,662 A | 1/1993 | Bartholomew et al. | |
| 5,257,980 A | 11/1993 | Van Antwerp et al. | |
| 5,342,319 A * | 8/1994 | Watson et al. | 604/180 |
| 5,390,671 A | 2/1995 | Lord et al. | |
| 5,568,806 A | 10/1996 | Cheney, II et al. | |
| 5,578,014 A | 11/1996 | Erez et al. | |
| 5,586,553 A | 12/1996 | Halili et al. | |
| 5,609,577 A * | 3/1997 | Haber et al. | 604/110 |
| 5,921,963 A * | 7/1999 | Erez et al. | 604/192 |
| 6,093,172 A | 7/2000 | Funderburk et al. | |
| 6,143,164 A | 11/2000 | Heller et al. | |
| 6,699,218 B2 | 3/2004 | Flaherty et al. | |
| 6,830,562 B2 | 12/2004 | Mogensen et al. | |
| 7,110,803 B2 | 9/2006 | Shults et al. | |
| 7,407,493 B2 * | 8/2008 | Cane' | 604/181 |
| 2007/0156094 A1* | 7/2007 | Safabash et al. | 604/164.12 |
| 2007/0191702 A1 | 8/2007 | Yodfat et al. | |
| 2008/0215035 A1 | 9/2008 | Yodfat et al. | |
| 2008/0281290 A1 | 11/2008 | Yodfat et al. | |
| 2008/0319414 A1 | 12/2008 | Yodfat et al. | |
| 2008/0319416 A1 | 12/2008 | Yodfat et al. | |
| 2010/0286467 A1 | 11/2010 | Pesach et al. | |

FOREIGN PATENT DOCUMENTS

| | | |
|---|---|---|
| WO | WO 95/13838 | 5/1995 |
| WO | WO 2006/123329 | 11/2006 |
| WO | WO 2007/010522 | 1/2007 |
| WO | WO 2007/093981 | 8/2007 |
| WO | WO 2008/012817 | 1/2008 |
| WO | WO 2008/029403 | 3/2008 |
| WO | WO 2008/038274 | 4/2008 |
| WO | WO 2008/065646 | 6/2008 |
| WO | WO 2008/078318 | 7/2008 |
| WO | WO 2009/056981 | 5/2009 |

OTHER PUBLICATIONS

Gecsedi et al., "Incorporating Alternative Therapies into Pain Management", *American Journal of Nursing* 101(4): 35-39 (2001).

Oumeish Youssef Oumeish, "The Philosophical, Cultural, and Historical Aspects of Complementary, Alternative, Unconventional, and Integrative Medicine in the Old World", *Archives of Dermatology* 134(11):1373-1386 (1998).

Ann F. Jacobson, "Intradermal normal saline solution, self-selected music, and insertion difficulty effects on intravenous insertion pain", *Journal of Acute and Critical Care* 28(2): 114-122 (1999).

M. Preyde, "Effectiveness of massage therapy for subacute low-back pain: a randomized controlled trial", *Journal of Canadian Medical Association* 162(13): 1815-1820 (2000).

P. Wall, "Pain: The Science of Suffering", *Weidenfeld & Nicholson*, London 1999.

Barnhill et al., "Using pressure to decrease the pain of intramuscular injections", *Journal of Pain and Symptom Management* 12(1): 52-58 (1996).

Chung et al., "An experimental study on the use of manual pressure to reduce pain in intramuscular injections", *Journal of Clinical Nursing* 11(4) 457-461 (2002).

Romano C.L. et al., "Pin-Pricks and Pins" Tricks: A New Method to Reduce Pin-Prick Pain of Intramuscular and Subcutaneous Injections, *Anesth Analg* 99(6): 1873 (2004).

Romano. C.L. et al., "A New Method to Reduce Pin-prick Pain of Intra-muscular and Subcutaneous Injections", *Minerva Anestesiol* 71(1 0): 609-615 (2005).

Mueller HL, "The practical use of a cooling device to inhibit the cutaneous pain of hypodermic injections", *N Engl J Med* 248(16): 692-693 (1953).

Hingson et al., "Hypodermic Injection Device", *JAMA* 184:319 (1963).

Written Opinion for PCT Application No. PCT/IL2008/000861.

International Search Report for PCT Application No. PCT/IL2008/000861.

* cited by examiner

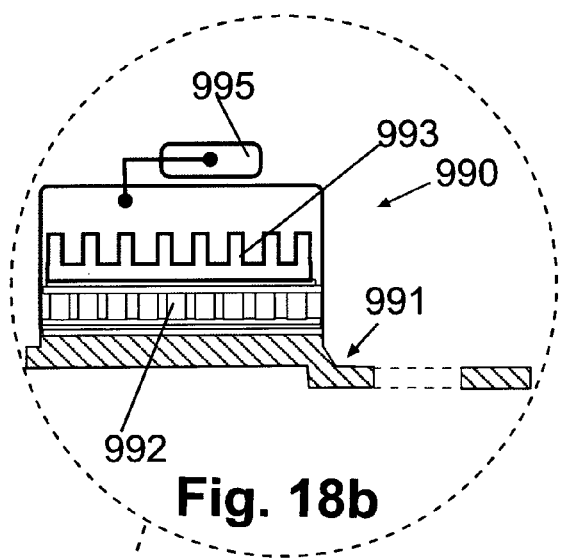
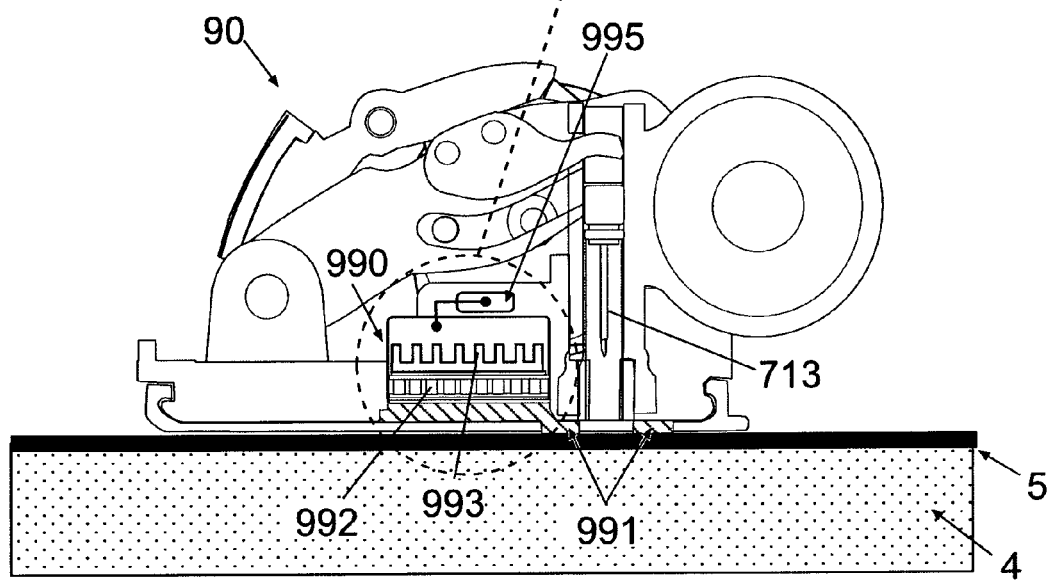
Fig. 18b
Fig. 18a

PORTABLE INFUSION PUMP WITH CANNULA INSERTER AND PAIN REDUCTION MECHANISM

CROSS-REFERENCE TO RELATED APPLICATIONS

The present application claims priority to the International Patent Application No. PCT/IL2008/000861, filed Jun. 25, 2008, and entitled "Portable Infusion Pump With Cannula Inserter And Pain Reduction Mechanism", which claims priority to U.S. Provisional Patent Application No. 60/937,163, entitled "Devices and Methods for Pain Reduction", U.S. Provisional Patent Application No. 60/937,214, entitled "Insertion Device for Inserting a Cannula into a Body", and U.S. Provisional Patent Application No. 60/937,155, entitled "Protector for Cannula and Penetrating Member Insertable in the Body of a Patient", all filed on Jun. 25, 2007, the disclosures of which are incorporated herein by reference in their entireties.

FIELD OF THE INVENTION

The present invention generally relates to medical devices, and particularly to devices that administer medication into the body of a patient and/or sense analyte levels in a bodily fluid. Some embodiments of the present invention relate to a cannula for delivery of a drug by an infusion pump and/or for continuous sensing of a body analyte. More particularly, some embodiments of the present invention relate to a cannula or a sensor and a method for manual or automatic insertion of a cannula or sensor into a body. Even more particularly, some embodiments of the present invention relate to a device and a method to reduce the pain induced by skin piercing during cannula or sensor insertion.

BACKGROUND OF THE INVENTION

Continuous subcutaneous delivery of medication or monitoring of a body analyte is often accomplished by the use of a cannula or a sensor, which generally remains in place for several days, hereinafter referred to as a "cannula". Diabetes patients may use such cannula positioned in a subcutaneous compartment for continuous delivery of insulin using pumps and/or for monitoring interstitial glucose levels by sensors. A combination of a tube, connecting an insulin pump to the cannula and a detachable connector is often referred to as an infusion set. Such infusion sets and modes of their insertion are disclosed, for example, in U.S. Pat. Nos. 4,755,173, 5,176,662 and 5,257,980, the disclosures of which are incorporated herein by reference in their entireties. Subcutaneous cannula insertion modes for continuous glucose monitoring are disclosed, for example, in U.S. Pat. Nos. 5,390,671, 5,568,806 and 5,586,553, the disclosures of which are incorporated herein by reference in their entireties.

Usually trans-cutaneous ("hypodermic") cannula insertion is carried out with a sharp metallic "penetrating member", which is withdrawn after piercing the skin. The hypodermic insertion is usually painful and requires considerable skill. Some patients are reluctant or hesitant to pierce their own skin, and thus encounter difficulties in proper cannula insertion. Such difficulties can be attributable to insufficient manual dexterity or alternatively to anxiety associated with anticipated discomfort as the needle pierces the skin. This problem can be especially significant when an insulin pump is used since misplacement of a cannula can cause kinking, incorrect insertion angle or incorrect cannula insertion depth leading eventually to cannula obstruction. Consequently delivery of insulin may be hampered thereby creating a life-threatening situation.

In an attempt to cope with this problem, automatic infusion set insertion devices ("inserters") were developed to assure correct placement of a cannula in the body, at a correct angle, while minimizing hazardous obstructions associated with cannula insertion. U.S. Pat. Nos. 6,093,172 and 6,830,562 disclose inserters comprising a spring-loaded mechanism for an automatic subcutaneous placement of infusion sets. These automatic inserters can be used with so-called "pager-like" pumps having long tubing, cannula and adhesive, altogether constituting an "infusion set". A new generation of portable infusion devices is the skin adherable pump which has no tubing, as for example disclosed in U.S. Pat. No. 6,699,218. After attaching the device to the user's skin a spring loaded cannula automatically emerges from the device's housing and pierces the skin. Unfortunately, neither an automatic inserter for a pager-like pump infusion set nor automatic insertion mode of a cannula emerging from a skin adherable pump employ a means for reducing the pain associated with skin piercing during cannula insertion.

Continuous glucose monitors are disclosed in U.S. Pat. Nos. 5,390,671 and 6,143,164, assigned to MiniMed and E. Heller & Company, respectively. These devices monitor glucose levels in the subcutaneous compartment by a sensor that is inserted manually or automatically as disclosed in U.S. Pat. No. 7,110,803, assigned to DexCom, in the same manner as a cannula for drug delivery. The above continuous glucose monitors, however, have no means for reducing the pain induced by skin piercing.

Thus, it would be desirable if a subcutaneous cannula, or a sensor, that is associated to a fluid delivery and/or analyte sensing device could be inserted in a precise and user-friendly manner as well as with minimal pain induced by skin piercing.

Pain is defined as an unpleasant sensation and emotional experience arising from actual or potential tissue damage. Undoubtedly, pain is an unpleasant sensation which we instinctively try to avoid. Injection and skin pricking during cannula insertion causes pain and discomfort to the user, and over the years various methods to reduce injection related pain have been explored. The use of hands is unquestionably the oldest, most universally utilized and probably most appreciated means for relieving pain (Nursing Ethics 1996; 3:165-176. American Journal of Nursing 2001; 101:35-39). Touching, massaging or manipulating areas that are painful, tense or tight has been used widely in homes and in hospitals (Archives of Dermatology 1998; 134(11):1373-1386. Journal of Acute and Critical Care 1999; 28(2):114-122. Journal of Canadian Medical Association 2000; 162(13):1815-1820). The gate control theory, which states that physical pain is not a direct result of activation of pain receptor neurons, but rather, its perception is modulated by interaction between different neurons, provides a framework for the mechanism of pain relief. C fibers, which conduct impulses responsible for provoking markedly unpleasant sensations, are inhibited at the dorsal horn of the spinal cord by input from the A delta fibers (Pain: the Science of Suffering Weidenfeld & Nicholson, London 1999). It is suggested that the so-called massage is effective in relieving the pain because of its stimulation of the large-diameter myelinated.

A delta fibers, which thereby increase the inhibitory tone and close the pain gates. Barnhill et al (Journal of Pain and Symptom Management 1996; 12: 52-58) reported that a subject group which received pressure prior to injection demonstrated a significant reduction in perceived pain intensity, and concluded that applying pressure before the injection was useful in reducing pain from an intramuscular injection. Applying pressure to the injection site is believed to increase the stimulation of A delta fibers, resulting in the increase of inhibition of transmission of C fibers by closing the gate. Joanne et al (Journal of Clinical Nursing 2002; 11(4) 457-461) demonstrated a significant difference in the perceived pain intensity for experimental and control conditions. Subjects who were applied with manual pressure before injections reported lower pain intensity scores, whilst those who were not treated with manual pressure before injections reported higher pain intensity scores. Romano & Cecca (Anesth Analg 2004; 99(6):1873. Minerva Anestesiol 2005; 71(10):609-15) showed that tactile stimulation with multiple blunt plastic pins pressed onto the skin at the injection site and during the injection procedure is able to reduce the reported pin prick pain after subcutaneous or intramuscular injection as compared to placebo. Nevertheless none of these mechanical means for pain alleviation is currently employed in cannula insertion devices associated with portable infusion or sensing devices, such as skin adherable infusion/sensing devices or skin adherable insulin pumps that contain a continuous glucose monitor.

Skin cooling is an additional means for reducing pain associated with hypodermic injections (N Engl J Med 1953; 248 (16): 692-3. JAMA 1963; 184:319). Various devices and methods are known in the related art for local cooling of skin, for example U.S. Pat. Nos. 2,746,264, 2,982,112, 3,327,713, 3,826,264, 4,614,191, 4,646,735, 5,578,014, and 5,921,963, the disclosures of which are incorporated herein by reference in their entireties. None of these cooling devices for pain alleviation are currently employed in cannula insertion devices associated with portable infusion or sensing devices, such as skin adherable infusion/sensing devices or skin adherable insulin pumps that contain a continuous glucose monitor.

Thus, it is desirable to provide a device capable of being used with portable infusion or sensing devices, e.g., skin adherable infusion and/or sensing devices, and capable of relieving pain associated with inserting a cannula and/or sensor into the body.

SUMMARY OF THE INVENTION

In some embodiments, the present invention relates to a device and a method for inserting a hypodermic cannula and/or sensor into the body of a patient, where the device includes a pain reduction means for reducing pain associated with such insertion. The insertion device is intended for use with a device for delivery of a therapeutic fluid into the body and/or for sensing a bodily analyte. In some embodiments, the insertion device applies pressure onto the skin of the patient/user. The insertion device can be fitted with a means for cooling the skin. In some embodiments, the fluid delivery device is an infusion pump ("dispensing patch unit") that can be connected to and disconnected from a cradle unit, where the cannula is inserted through the cradle unit into the body and can remain rigidly connected to the cradle unit. In some embodiments, the fluid delivery device includes a skin adherable analyte monitoring device that can be connected to and disconnected from the cradle unit having a sensor that can be inserted through the cradle unit into the body and can remain rigidly connected to the cradle unit. The analyte monitoring device can employ a single cannula/sensor means.

In some embodiments, the cannula assembly includes the following features:
a cannula coupled with a penetrating member to facilitate skin piercing;
the cannula and the penetrating member are concealed and guarded by a protective means ("protector") to avoid unintentional piercing (the cannula, the penetrating member and the protector can be referred to as the "cannula cartridge unit");
the cannula cartridge unit can be loaded into an automatic insertion means ("inserter");
the inserter includes the pain reduction means that applies pressure onto the skin before and/or during cannula insertion, and/or cools the skin before and/or during cannula insertion;
the cannula and the penetrating member can be fired into the body by an inserter; and,
the penetrating member can be retracted back into the protector and then disposed.

In some embodiments, the cannula cartridge unit includes a cannula that can be automatically inserted into the body and used for delivery of medication to the patient using the dispensing patch unit. The cannula can be inserted using an automatic inserter fitted with the pain reduction means. The sensor (for continuous glucose monitoring) also can be inserted automatically along with the cannula. In some embodiments, the cannula deployed within the cannula cartridge unit can be inserted into the body at any desired depth, i.e., the patient can choose the desired cannula length. The cannula can also be deployed at any desired angle. The cannula can be precisely aligned relative to the cradle unit and remain connected to the cradle unit after insertion.

In some of the embodiments, the present invention relates to a device and a method for alleviating pain associated with insertion of a hypodermic cannula. In some embodiments, to alleviate pain, an array of blunt pins applies pressure onto the skin in the vicinity of a cannula insertion site. The blunt pins protrude from the cannula inserter that is brought in contact with the skin before cannula insertion. The inserter is intended for automatic or manual insertion of the cannula that is intended for use with the fluid delivery device. In some embodiments, the cannula and the penetrating member can be contained within a protector constituting the "cannula cartridge unit". During insertion the cannula and the penetrating member are protracted from the protector, the cannula remains in the body and the penetrating member can be retracted back into the protector and then disposed. The cannula cartridge unit can be loaded into the inserter, which is fitted with protrusions for pain reduction. The infusion device can be a remote controlled skin adherable patch pump (referred to also as a "dispensing patch unit") allowing programmed fluid delivery. The infusion device can also include a continuous analyte level monitor. In some embodiments, the delivered fluid is insulin and the monitored analyte is glucose.

In some embodiments, the device includes a remote control and the following units:
1. a dispensing patch unit having
   i. a reusable part containing a driving mechanism, a printed circuit board ("PCB") and electronics, and
   ii. a disposable part containing a reservoir, a delivery tube and an outlet port with a connecting lumen;
2. a cradle unit for allowing connection and reconnection of the dispensing patch unit to the body, where the cradle includes a tubular passage (referred to further as "well") to allow cannula penetration into the skin and can be fitted with an adhesive sheet to allow attachment to the body; the well can be surrounded by a plurality of pores allowing the protrusions provided at the inserter to penetrate the cradle and apply pressure onto the skin;
3. a cannula cartridge unit which includes a cannula, a penetrating member, and a protector; the cannula can be fitted with a cannula hub having a rubber septum, where the septum can be repeatedly pierced by the connecting lumen provided in the disposable part of the dispensing patch unit.

A process for setting up the above system includes the following steps:
1. fill reservoir with fluid;
2. assemble the dispensing patch unit from two parts (a disposable part and a reusable part);
3. adhere the cradle unit (in some embodiments, this step can be carried out after connecting an inserter to the cradle unit);
4. insert cannula, which includes the following steps:
   i. load the cannula cartridge unit into the inserter, which is fitted with the pain reduction means (e.g., a plurality of protrusions),
   ii. connect the inserter with protrusions to the cradle unit such that the protrusions penetrate the cradle and touch the skin,
   iii. apply pressure on the inserter for few seconds such that the pressure is spread over the protrusions,
   iv. automatically or manually advance the cannula along with the penetrating member through the cradle unit towards the body, then pierce the skin, and dispose the cannula in the subcutaneous compartment,
   v. automatically or manually withdraw the penetrating member from the body into the protector while the cannula is secured at the cradle unit;
5. connect dispensing patch unit to the cradle unit such that the connecting lumen emerges from the outlet port provided in the disposable part, pierces the cannula hub's rubber septum and maintains fluid communication between reservoir, delivery tube, cannula and subcutaneous tissue; and
6. program fluid delivery using a remote control unit.

In some embodiments, the cannula which delivers the fluid (e.g., insulin) into the body includes a sensor for monitoring a body analyte (e.g., glucose). Fluid delivery may be adjusted according to sensor inputs (semi or fully closed-loop mode). In some embodiments, the dispensing patch unit can include both a cannula for fluid delivery and a sensor for analyte sensing, wherein both can be inserted into the body using the above inserter.

In some embodiments, the inserter can be fitted with a cooling means. The cooling means can include a gas container stored within the inserter's housing for releasing a cooling gas after the inserter is connected to the cradle unit and attached to the body. In some embodiments, the cooling means may be provided with thermoelectric modules, which are solid-state heat pumps that operate according to the Peltier effect. The thermoelectric modules may be activated upon connection of the inserter to the cradle unit.

According to some embodiments, an inserter and a method to alleviate the pain associated with skin piercing are provided for manual or automatic insertion of a hypodermic cannula. The cannula can be used for infusion devices and portable infusion pumps (e.g., insulin pumps).

According to some embodiments, an inserter and a method to alleviate the pain associated with skin piercing are provided for manual or automatic insertion of a hypodermic sensor. The sensor can be used for continuous sensing of a subcutaneous analyte (e.g., glucose).

According to some embodiments, an inserter and a method for painless insertion of the cannula are provided for automatic or manual insertion of a cannula contained within a cannula cartridge unit that can be used with a skin adherable dispensing pump.

According to some embodiments, an inserter and a method for painless insertion of the sensor are provided for automatic or manual insertion of a sensor contained within a cannula cartridge unit that can be used in association with a skin adherable continuous analyte monitoring means.

According to some embodiments, an inserter is provided for inserting a cannula and a sensor contained within a cannula cartridge unit for use in association with a skin adherable pump having analyte sensing and fluid dispensing capabilities and that fluid dispensing may be adjusted according to analyte sensing (semi or fully closed-loop mode). A method of painless insertion of the cannula and the sensor is also provided.

According to some embodiments, an inserter and a method for painlessly inserting a cannula and a sensor contained within a cannula cartridge unit are provided, where the cannula is used for insulin delivery and the sensor continuously monitors glucose levels.

According to some embodiments, an inserter and a method for painless cannula insertion are provided, where the inserter can be loaded with a cannula cartridge unit which can be easily removed.

According to some embodiments, an inserter and a method for painless cannula insertion are provided, where the inserter can be loaded with a cannula cartridge unit which may be easily handled and has a griping means that facilitates loading and unloading.

In some embodiments, the inserter includes protrusions. The protrusions can penetrate into pores surrounding the cradle unit's well. Prior to cannula insertion the user presses on the inserter and consequently applies pressure onto those regions of the skin that surround the well. In some embodiments, the inserter is preloaded with a cannula cartridge unit and a cradle unit. After spring loading, the user may attach the cradle unit to the skin and pushes a release button. In some embodiments, a spring-loaded flywheel forcefully pushes the cannula and penetrating member out of the protector through the well and into the body. Consecutively, the penetrating member is automatically retracted back into the protector and a cannula hub is rigidly secured at the well. Finally, the inserter is removed from the cradle unit and the protector (with the penetrating member inside) is unloaded and disposed of In some embodiments, the inserter for painless cannula insertion can be loaded with a plurality of cannula cartridge units.

In some embodiments, the inserter can be disposable or reusable. In the disposable configuration, the inserter is preloaded with a cannula cartridge unit and, after its insertion, the used protector (along with the penetrating member) remains within the inserter housing, which may then be discarded together with the inserter.

In some embodiments, the insertion can be done automatically and retraction of penetrating needle can be done manually. In some embodiments, the inserter enables alignment of the cannula with the cradle unit. In some embodiments, the inserter also allows cannula insertion at any desired penetration angle. Also, in some embodiments the inserter allows cannula insertion at any desired depth, i.e., the patient can choose the cannula length to correspond with the desired depth.

In some embodiments, the inserter for painless cannula insertion includes safety means for preventing inadvertent or premature insertion. The safety means includes a specific orientation of the cannula cartridge unit within the inserter to avoid misplacement.

According to some embodiments, a method for painless manual cannula insertion is provided in which a cannula cartridge unit is directly attached to the cradle unit and the cannula and penetrating member are pushed through the well into the body with the aid of a dedicated rod (or alike). After insertion, the protector is removed from the cradle unit and the penetrating member is manually retracted and disposed of. In some embodiments, a pencil-like device facilitates penetrating member retraction back into the protector prior to the protector's removal from the cradle unit.

BRIEF DESCRIPTION OF THE DRAWINGS

FIGS. 18a-c are cross-sectional and bottom views of an exemplary inserter fitted with a thermoelectric cooler (TEC), according to some embodiments of the present invention.

DETAILED DESCRIPTION OF THE DRAWINGS

Figure 1A:
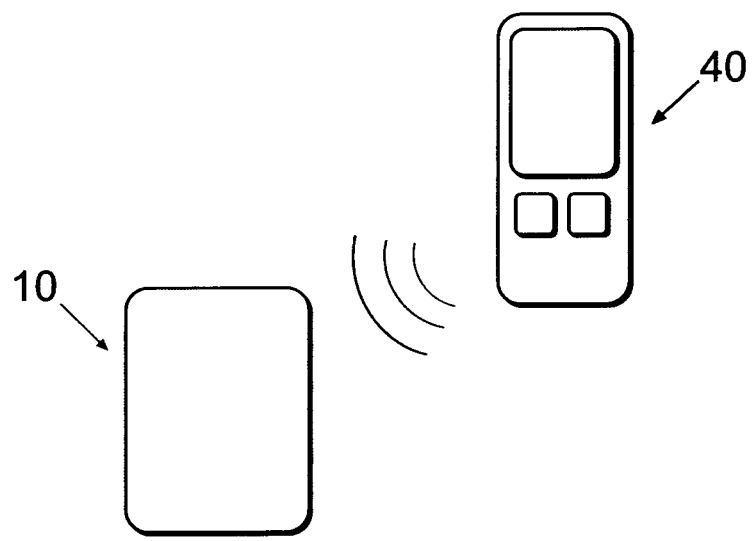
FIGS. 1a-c show an exemplary single-part dispensing unit, two-part dispensing unit, and remote control unit, according to some embodiments of the present invention.

For the purposes of promoting an understanding of the embodiments described herein, reference will be made to embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a drug" includes a plurality of such drugs, as well as a single drug, and equivalents thereof known to those skilled in the art, and so forth.

The examples provided herein are illustrative, but not limiting, of the methods, devices, and compositions of the present invention. Other suitable modifications and adaptations of the variety of conditions and parameters normally encountered and that are obvious to those skilled in the art are within the spirit and scope of the embodiments.

A skin adherable insulin delivery device was disclosed a co-owned, co-pending International Patent Application No. PCT/IL07/000932, filed Jul. 24, 2007, claiming priority to U.S. Provisional Patent Application No. 60/833,110, filed Jul. 24, 2006, and U.S. Provisional Patent Application No. 60/837,877, filed Aug. 14, 2006, and also disclosed in a co-owned/co-pending U.S. patent application Ser. No. 12/004,837, and International Patent Application No. PCT/IL07001578, both filed Dec. 20, 2007 and both claiming priority to U.S. Provisional Patent Application No. 60/876,679, filed Dec. 22, 2006. The disclosures of the above applications are incorporated herein by reference in their entirety. This device contains a remote control unit and a skin adherable unit, and may be referred to as "dispensing patch unit". The dispensing patch unit is coupled with a unique cannula apparatus, which does not require an infusion set and long tubing. The cannula apparatus allows the patient to choose the desired depth and angle for cannula insertion. In some embodiment of the device a "cradle unit" is provided. The cradle unit is configured as a sheet with an adhesive layer that is attached to the skin before cannula insertion, and it is used to allow connection and disconnection of the dispensing patch unit to and from the body. The cannula is inserted through the cradle unit into the skin and remains rigidly connected to cradle unit after insertion. The penetrating member (metallic sharp needle) is then retracted and can be disposed.

Co-owned/co-pending International Patent Application No. PCT/IL08/000860and U.S. patent application Ser. No. 12/215,255, , claiming priority to U.S. Provisional Patent Application No. 60/937,214, entitled "Insertion Device for Inserting a Cannula into a Body",U.S. Provisional Patent Application No. 60/937,155, entitled "Protector for Cannula and Penetrating Member Insertable in the Body of a Patient", and U.S. Provisional Patent Application No. 60/937,163, entitled "Devices and Methods for Pain Reduction",all filed Jun. 25, 2007, the disclosures of which are incorporated herein by reference in their entireties, disclose a device ("inserter") and a method for automatic insertion of the cannula associated with a skin adherable dispensing device. The inserter is preloaded with a cradle unit and with a "cannula cartridge unit" (which includes a cannula, a penetrating member and a protector). The user attaches the cradle unit to the skin and consecutively fires the cannula through the cradle unit into the body. The penetrating member is then retracted manually or automatically and can be disposed.

Continuous glucose monitors are disclosed in a co-owned/co-pending International Patent Application No. PCT/IL07/001096, filed Sep. 5, 2007, claiming priority to U.S. Provisional Patent Applications No. 60/842,869, filed Sep. 6, 2006, and International Patent Application No. PCT/IL07/001177, filed Sep. 25, 2007, claiming priority to U.S. Provisional Patent Application No. 60/848,511, filed Sep. 29, 2006. The disclosures of the above applications are incorporated herein by reference in their entireties.

The further description of the invention deals mostly with insertion of a cannula. It should be borne in mind however that this description may be equally used for insertion of a sensor for sensing bodily analyte or any other subcutaneously insertable element.

Figure 1B:
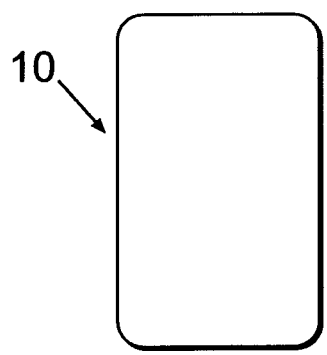
Figure 1C:
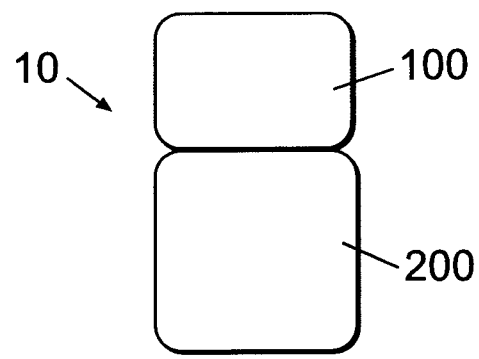

FIG. 1a shows an exemplary fluid delivery device having a dispensing patch unit (10) and a remote control unit (40), according to some embodiments of the present invention. The dispensing patch unit (10) can include a single part (FIG. 1b) or two parts (FIG. 1c), e.g., a reusable part (100) and a disposable part (200). The dispensing unit (10) communicates with the remote control unit (40) that can forward commands, receive and process instructions from the dispensing unit (10), etc. The remote control unit (40) can include a display and a plurality of buttons to control operation of the units (10) and (40). The units (10) and (40) can communicate with a wireless, wired, wire line, RF or any other type communication. The unit (40) can be a personal computer, a laptop, an iPod, a PDA, a cellular telephone, a remote control, or any other suitable device. In some embodiments, fluid delivery can be programmed solely by a remote control unit (40) having a bidirectional communication link with the transceiver provided in the dispensing unit (10).

Figure 2A:
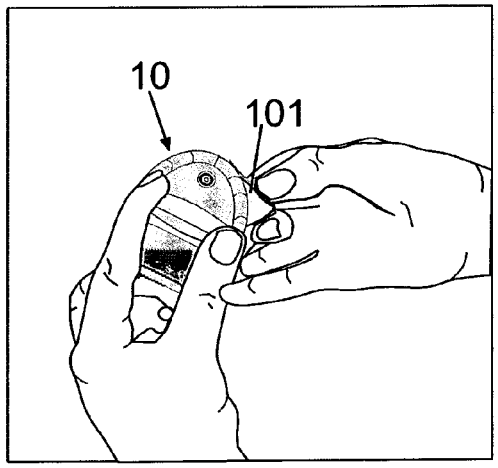
FIGS. 2a-c show an exemplary dispensing unit adhered directly to the skin of a patient, according to some embodiments of the present invention.
Figure 2B:
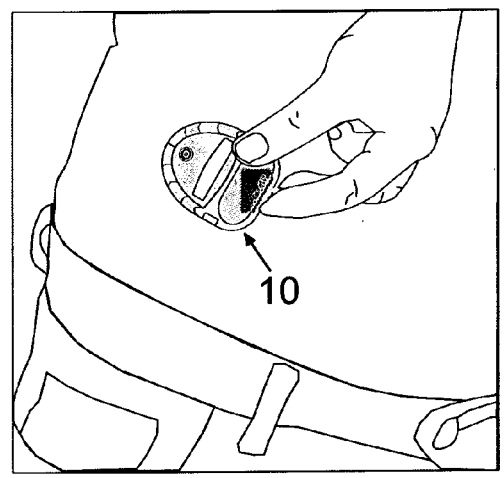
Figure 2C:
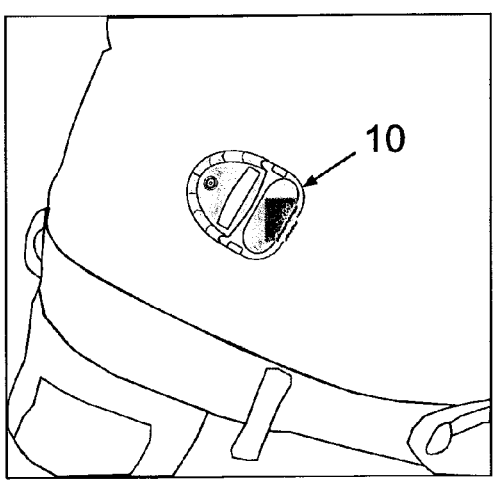

FIGS. 2a-c show an exemplary direct adherence of the dispensing patch unit (10) to the skin (5) of the patient/user. FIG. 2a shows peeling of an adhesive protective sheet (101) from the dispensing patch unit (10). FIG. 2b shows adherence of the dispensing patch unit (10) to the skin (5). FIG. 2c shows the dispensing patch unit (10) being adhered to the skin (5) and ready for operation.

Figure 3A:
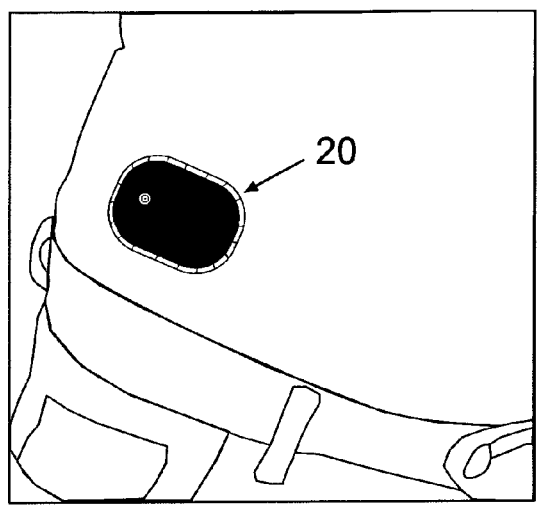
FIGS. 3a-c show an exemplary connection of the dispensing unit to a cradle unit, according to some embodiments of the present invention.
Figure 3B:
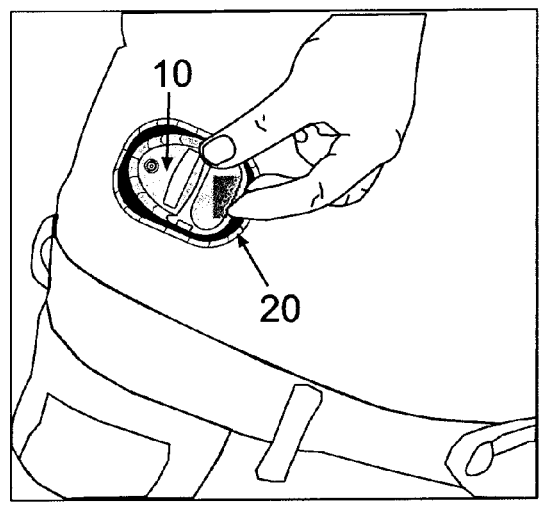
Figure 3C:
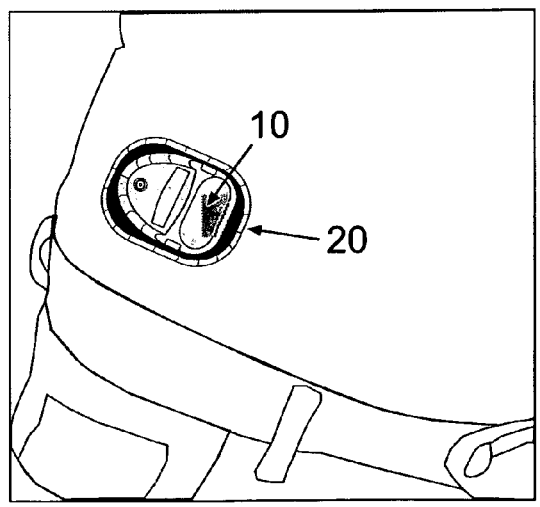

FIGS. 3a-c show an exemplary dispensing device which is provided with a cradle unit (20), according to some embodiments of the present invention. The cradle unit can be initially adhered to the skin (5) and then the dispensing patch unit (10) can be connected to and/or disconnected from the cradle unit (20) upon patient's discretion. An example of the device employing a cradle unit is disclosed in a co-pending/co-owned U.S. patent application Ser. No. 12/004,837, and International Patent Application No. PCT/IL07001578, both filed Dec. 20, 2007 and both claiming priority to U.S. patent application Ser. No. 60/876,679, filed Dec. 22, 2006.

FIG. 3a shows the cradle unit (20) being adhered to the skin (5), according to some embodiments. FIG. 3b shows connection of the dispensing patch unit (10) to the adhered cradle unit (20), according to some embodiments. FIG. 3c shows the dispensing patch unit (10) being connected to the cradle unit (20) and ready for operation, according to some embodiments.

Figure 4A:
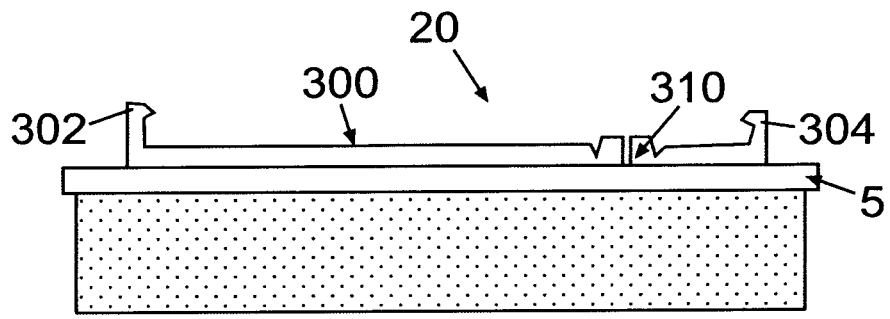
FIGS. 4a-c schematically show an exemplary cradle unit, according to some embodiments of the present invention.
Figure 4B:
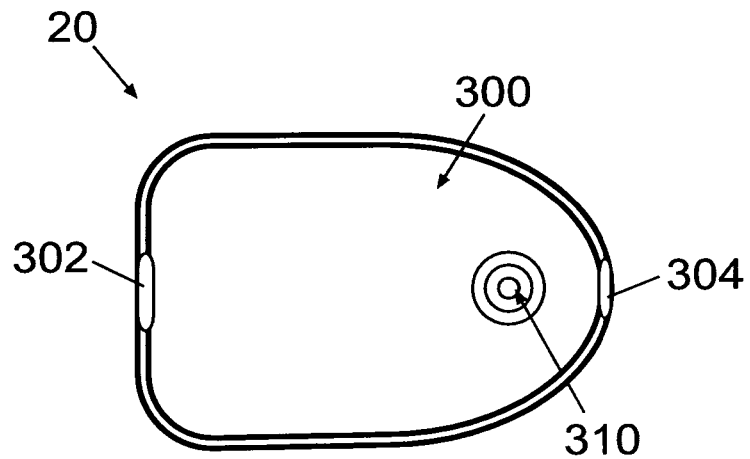

FIGS. 4a-b show side and upper views (respectively) of a cradle unit (20). The cradle unit (20) includes the following elements:

a cradle base (300) configured as a flat sheet with an adhesive layer facing the skin (5) and anchoring means (302), (304) on its upper side for connecting and/or disconnecting the inserter and the dispensing patch unit;

a well (310) configured as a tubular protrusion emerging upwardly from the cradle base (300) to allow alignment and appropriate connection between the cradle unit (20) and the inserter, and between the cradle unit (20) and the dispensing patch unit; the well constitutes a tubular passage through which fluid is delivered by the dispensing patch unit to the body.

Figure 4C:
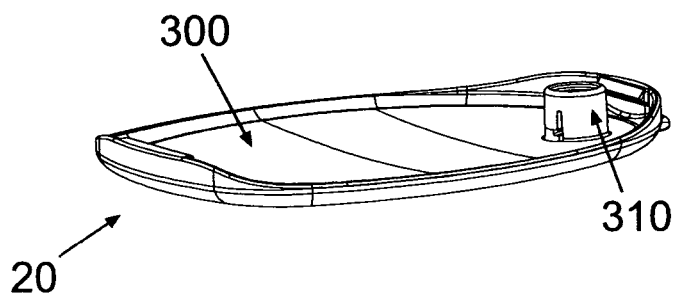

FIG. 4c shows the exemplary cradle unit (20) having the cradle base (300) and the well (310).

Figure 5:
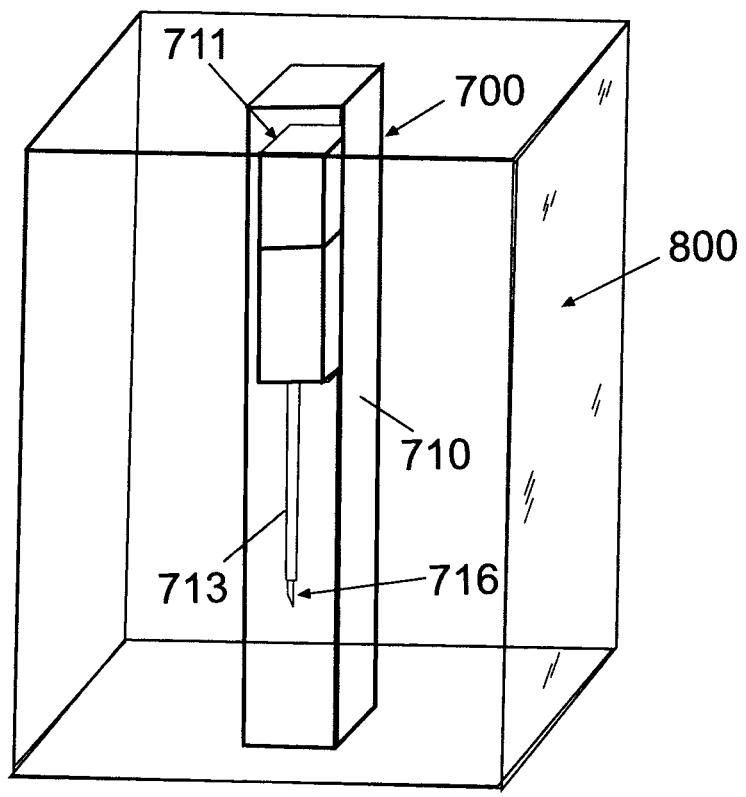
FIG. 5 schematically shows an exemplary inserter loaded with a cannula cartridge unit, according to some embodiments of the present invention.

FIG. 5 shows an exemplary inserter (800) loaded with a cannula cartridge unit (700), according to some embodiments of the present invention. The cannula cartridge unit (700) includes a protector (710) and a penetrating cartridge (711). The penetrating cartridge (711) includes a cannula (713) used for fluid (e.g., insulin) delivery from the dispensing patch unit to the body and/or for analyte (e.g., glucose) sensing. The penetrating cartridge can include a penetrating member (716) that pierces the skin and facilitates insertion of the cannula (713). The protector (710) can be configured as a protective cover that conceals and guards the cannula (713) and the penetrating member (716). Thus, the user is protected from unintentional skin piercing. As can be understood by one skilled in the art, the shape and size of the protector (710) are not limited to any specific shape and size, and the protector (710) can also contain a plurality of cannulae.

The inserter (800) allows either automatic or manual protraction of the cannula (713) and the penetrating member (716) from a protector (710) and into the user's body (i.e., a hypodermic cannula insertion). Once the cannula and the penetrating member are protracted from the protector (710), the penetrating member (716) pierces the skin (5), thereby allowing insertion of the cannula (713). After insertion, the cannula (713) continues to remains in the body and the penetrating member (716) is retracted back into the protector (710). In this case, the process terminates with the unloading of the protector (710) (with the penetrating member (716) disposed inside) from the inserter (800) and disposal of the item.

Where the protector (710) is not employed, the penetrating cartridge (711) may be contained within the inserter (800) itself. Thus, the insertion process can be carried out as disclosed in co-owned, co-pending International Patent Application No. PCT/IL07/001454, filed Nov. 26, 2007, claiming priority to U.S. Provisional Patent Application No. 60/861, 345, filed Nov. 28, 2006, and U.S. patent application Ser. No. 12/004,837, and International Patent Application No. PCT/IL07001578, both filed Dec. 20, 2007 and both claiming priority to U.S. Provisional Patent Application No. 60/876,679, filed Dec. 22, 2006, the disclosures of which are incorporated herein by reference in their entireties.

Figure 6A:
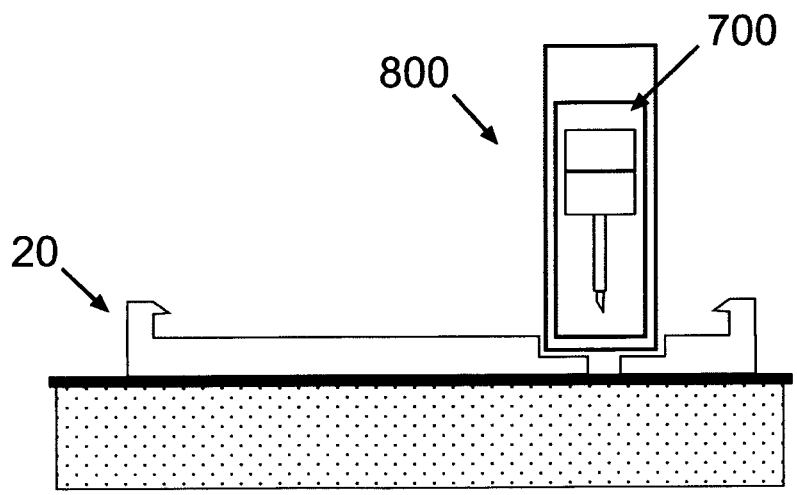
FIGS. 6a-c show an exemplary inserter connected to the cradle unit (as shown in FIG. 6a), a well assembly (as shown in FIG. 6b), and an infusion set (as shown in FIG. 6c), according to some embodiments of the present invention.
Figure 6B:
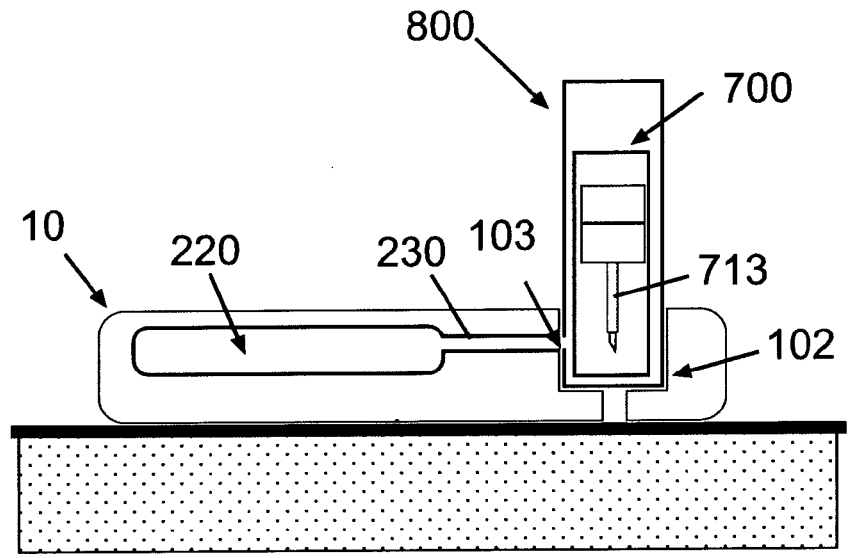
Figure 6C:
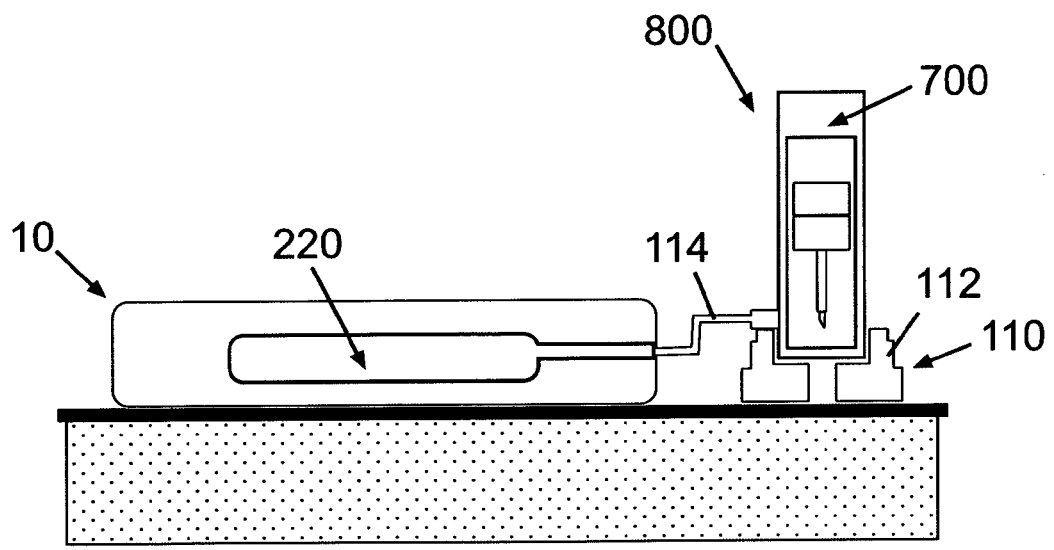

The inserter may be used in conjunction with the cradle unit or in conjunction with any skin adherable dispensing patch unit, which delivers the fluid using a well assembly or an infusion set. The inserter can also be connected to an infusion set used with a non-adherable dispensing device (e.g.," pager-like"). FIG. 6a shows an inserter (800) loaded with a cannula cartridge unit (700) and connected to a cradle unit (20), according to some embodiments of the present invention. After the insertion process is completed, the inserter (800) may be disconnected from the cradle unit (20) and a dispensing patch unit (not shown in FIG. 6a) may be connected to the cradle unit (20). FIG. 6b shows the inserter (800) loaded with a cannula cartridge unit (700) and connected to a well assembly (102) which may be employed in a single-part dispensing patch unit (10) or in a two-part dispensing patch unit, according to some embodiments of the present invention. The well assembly (102) can have an inlet port (103) on its side to allow the passage of the dispensed fluid from the delivery tube (230) to the cannula (713) through a lateral opening (not shown in FIG. 6b) made in the. cannula (713). FIG. 6c shows the inserter (800) loaded with a cannula cartridge unit (700) and connected to an infusion set (110), according to some embodiments of the present invention. The infusion set includes a hub (112) and a short connecting tube (114) extending from the dispensing patch unit (10) to a proximate insertion site. The connecting tube (114) is in fluid communication with a reservoir (220) located in the dispensing patch unit.

Figure 7A:
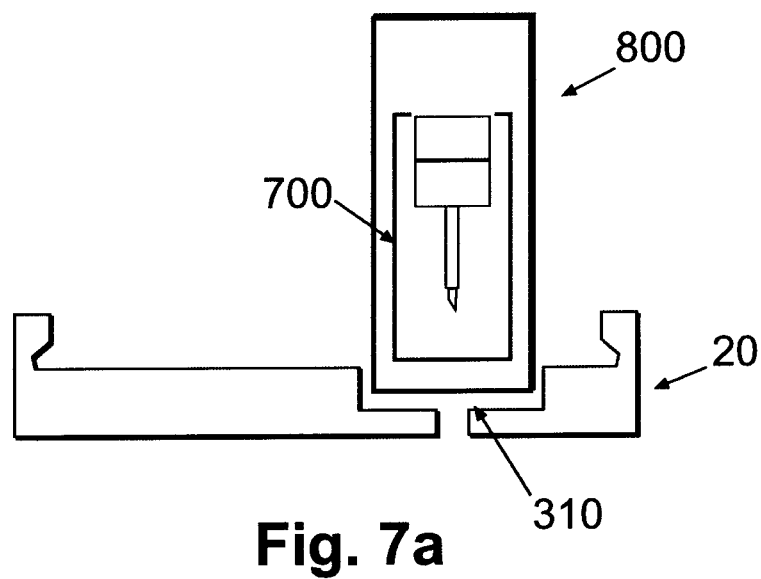
FIGS. 7a-b show various types of exemplary inserters loaded with a cannula cartridge unit, according to some embodiments of the present invention.
Figure 7B:
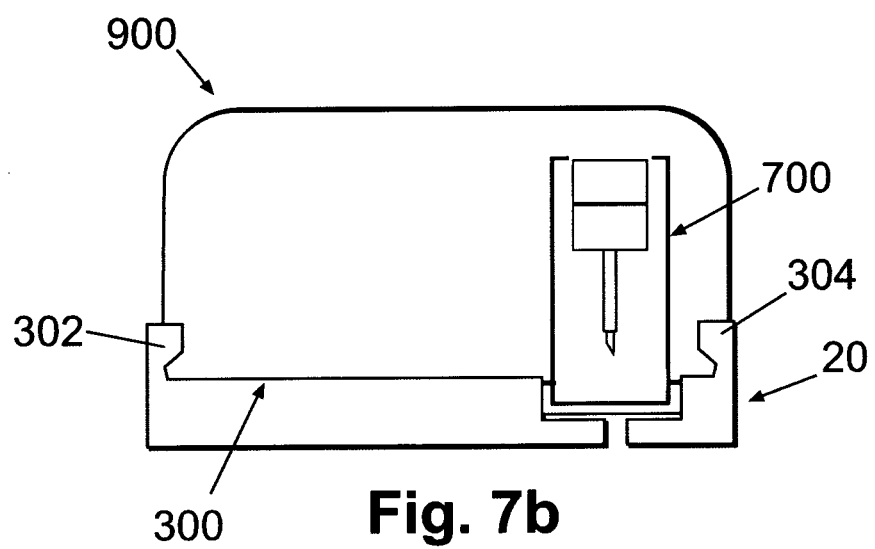

Various types of inserters may be employed for insertion of the cannula into the body. FIG. 7a schematically shows the inserter (800) having a shape of a pen and connected to the cradle unit (20) via the well (310), according to some embodiments of the present invention. FIG. 7b schematically shows an inserter (900) having a shape of a computer mouse (hereinafter, referred to as "mouse-like") and connected to the cradle unit (20) using anchoring means (302), (304) provided on an upper side of the cradle base (300), according to some embodiments of the present invention. The above are two examples of the various types of inserters, which may be employed for cannula insertion. As can be understood by one skilled in the art, other types of inserters exist for inserting cannula into the body of the patient/user. All pain reduction means described herein or known in the related art may be employed in conjunction with various inserter types.

Figure 8A:
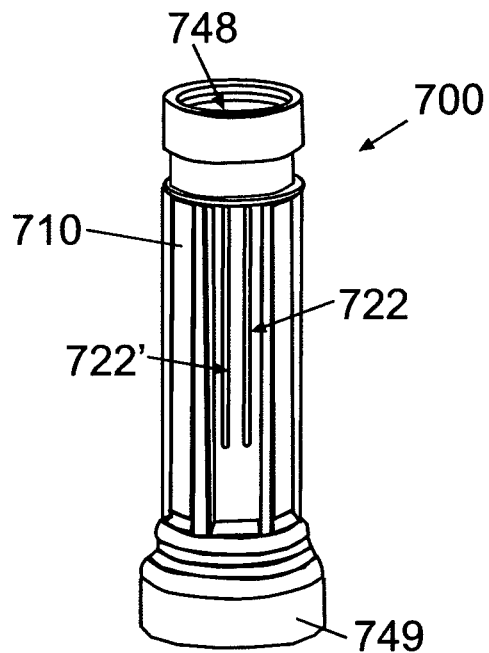
FIGS. 8a-b are perspective and cross-sectional views of an exemplary cannula cartridge unit, according to some embodiments of the present invention.

FIG. 8a is a perspective view of the cannula cartridge unit (700) having the protector (710) covering the cannula and the penetrating member (not shown in FIG. 8a), according to some embodiments of the present invention. In some embodiments, the protector includes an opened upper end (748) and an opened bottom end (749). The opened bottom end (749) of the protector (710) is dimensioned and configured to match the configuration and size either of the well assembly of the dispensing unit, or of the infusion set hub, or of the well of the cradle unit. Cannula insertion can be carried out by thrusting the penetrating cartridge manually or automatically using a dedicated means. Such dedicated means may be either a rod for pushing the penetrating cartridge through the protector's opened upper end (748). Alternatively, the dedicated means can be one or more engagement hooks for forcibly displacing the penetrating cartridge through one or more longitudinal slits (722), (722') provided in the lateral wall of the protector (710), as will be explained below. A single protector (having defined dimensions) may accommodate cannulae or sensors having various shapes and lengths, as discussed in co-owned, co-pending U.S. patent application Ser. No. 12/215,219and International Patent Application No. PCT/IL08/000859, claiming priority to U.S. Provisional Patent Application No. 60/937,155, entitled "Protector for Cannula and Penetrating Member Insertable in the Body of a Patient", U.S. Provisional Patent Application No. 60/937,214, entitled "Insertion Device for Inserting a Cannula into a Body", and U.S. Provisional Patent Application No. 60/937,163, entitled "Devices and Methods for Pain Reduction", all filed Jun. 25, 2007, the disclosures of which are incorporated herein by reference in their entireties. Thus, the same inserter (not shown in FIG. 8a) can be used for inserting cannulae or sensors having various shapes and lengths.

Figure 8B:
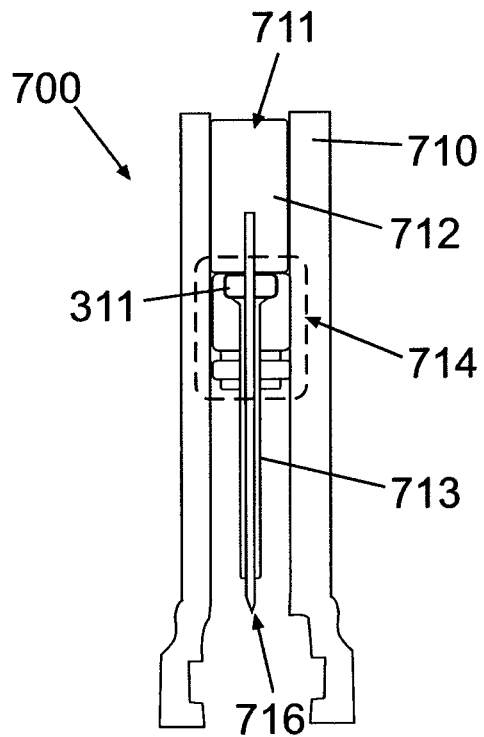

FIG. 8b is a cross-sectional view of the exemplary cannula cartridge unit (700) having the protector (710) and the penetrating cartridge (711). In some embodiments, the penetrating cartridge (711) includes a penetrating member (716) having a grip portion (712) located at the blunt end of the penetrating member (716) and the cannula (713). In some embodiments, the penetrating cartridge (711) includes a cannula hub (714), which is attached to the cannula (713) and contains a rubber septum (311) for maintaining the upper opening of the cannula (713) sealed after the cannula has been inserted into the body of the patient/user and the penetrating member (716) has been retracted. The septum (311) can be pierced repeatedly using a connecting lumen (not shown in FIG. 8b) provided in the disposable part of the dispensing patch unit. The connecting lumen maintains fluid communication between the reservoir (not shown in FIG. 8b) and the cannula (713).

FIGS. 9a-g are cross-sectional views of the exemplary inserter (800) loaded with a cannula cartridge unit (700) during cannula insertion process, according to some embodiments of the present invention. The insertion can be carried out manually. The cannula cartridge unit (700) can also be used as a stand-alone item, in which case the inserter (800) is not be used, as discussed in co-owned, co-pending U.S. patent application Ser. No. 12/215,219 and International Patent Application No. PCT/IL08/000859, claiming priority to U.S. Provisional Patent Application No. 60/937,155, entitled "Protector for Cannula and Penetrating Member Insertable in the Body of a Patient", U.S. Provisional Patent Application No. 60/937,214, entitled "Insertion Device for Inserting a Cannula into a Body", and U.S. Provisional Patent Application No. 60/937,163, entitled "Devices and Methods for Pain Reduction", all filed Jun. 25, 2007, the disclosures of which are incorporated herein by reference in their entireties.

Figure 9A:
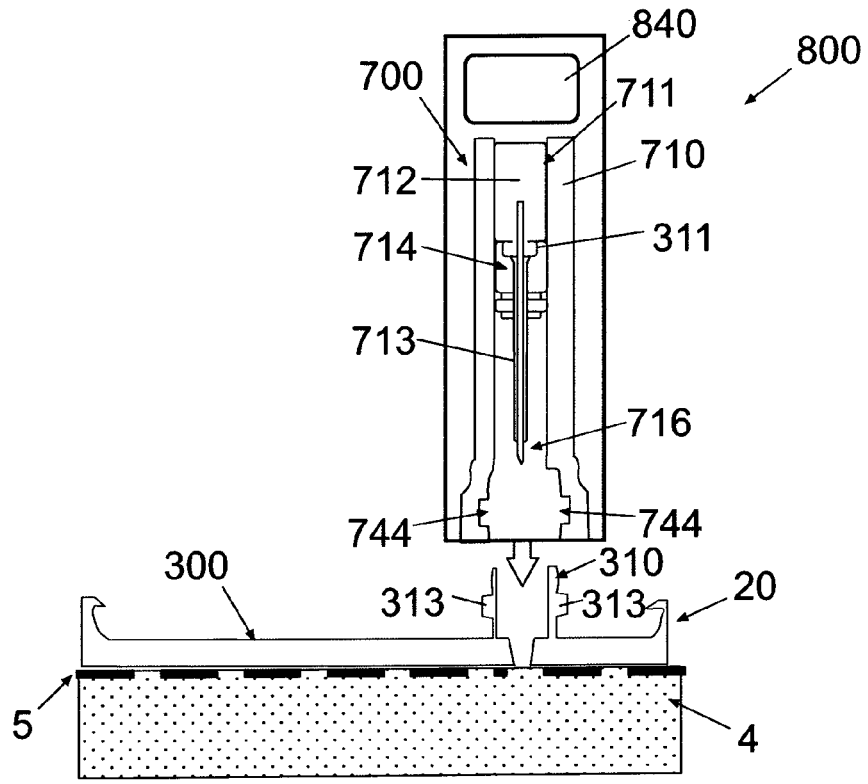
FIGS. 9a-g are cross-sectional views of an exemplary cannula insertion process, according to some embodiments of the present invention.
Figure 9B:
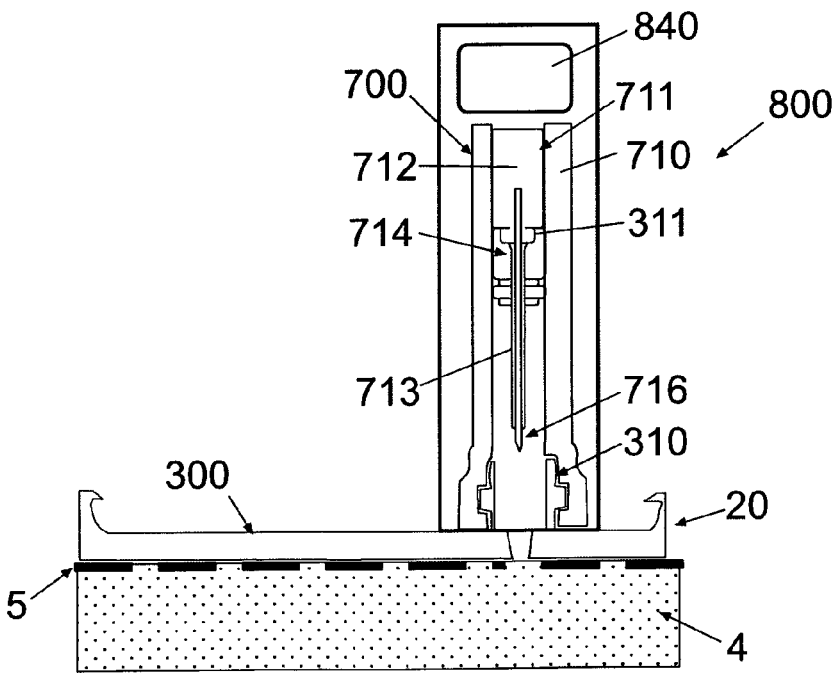
Figure 9C:
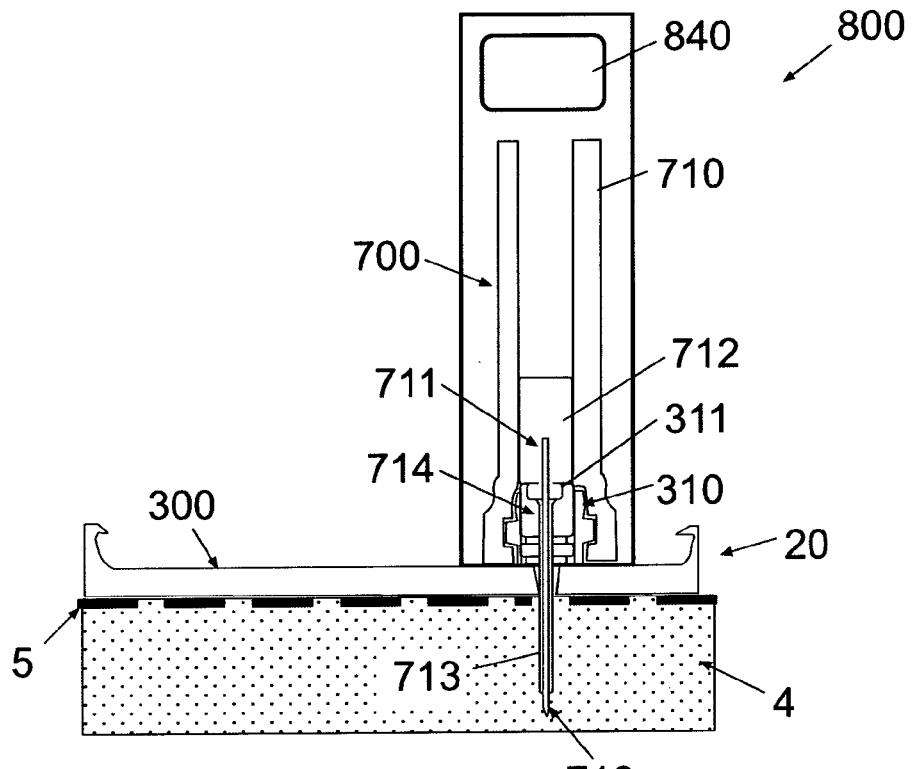

FIG. 9a shows the inserter (800) prior to connection to the skin adhered cradle unit (20), according to some embodiments of the present invention. The cradle unit (20) includes the well (310) disposed in the base (300) and having a snapping engagement mechanism with at least one resistance loaded latch (313). The cannula cartridge unit (700)includes at least one notch or recess (744) that corresponds and is configured to accommodate insertion of the latch (313). As discussed above, the cannula cartridge unit (700) is placed over the well (310),thereby snapping the notch (744) over the latch (313) and therefore locking the unit (700) to the well (310). As can be understood by one skilled in the art, other ways of securing the unit (700) to the well (310) are possible. In some embodiments, the cannula cartridge unit (700) can be only placed over a well (310) without being connected to the well (310). The connection between the cannula cartridge unit (700) and the well (310) when the unit (700) is brought toward the well (310) as illustrated by the arrow in FIG. 9a. In some embodiments, the connection is established between the inserter (800) and the cradle unit (300). The cannula cartridge unit (700) can be placed over the well, or it may not come in contact with the cradle unit (300) at all. The inserter (800) also includes a displacement mechanism (840) disposed in the inserter housing. The displacement mechanism (840) is configured to release the cannula (713) and the penetrating member (716) toward the body of the patient. Additionally, the displacement mechanism (840) can be configured to allow retraction of the penetrating member (716) once the cannula (713) has been secured into the body of the patient. Exemplary displacement mechanisms are discussed in co-owned, co-pending International Patent Application No. PCT/IL08/000860and U.S. patent application Ser. No. 12/215,255, claiming priority to U.S.Provisional Patent Application No. 60/937,214, entitled "Insertion Device for Inserting a Cannula into a Body",U.S. Provisional Patent Application No. 60/937,155, entitled "Protector for Cannula and Penetrating Member in the Body of a Patient", and U.S. Provisional Patent Application No. 60/937,163, entitled "Devices and Methods for Pain Reduction", all filed Jun. 25, 2007, the disclosures of these applications are incorporated herein by reference in their entireties. FIG. 9b shows the inserter (800) connected to the cradle unit (20) and being ready for operation. FIG. 9c shows the cannula (713) and penetrating member (716) being inserted into the subcutaneous tissue (4) of the patient/user. The penetrating cartridge (711) may be displaced downwardly either manually or automatically using the inserter's displacement mechanism (840).

Figure 9D:
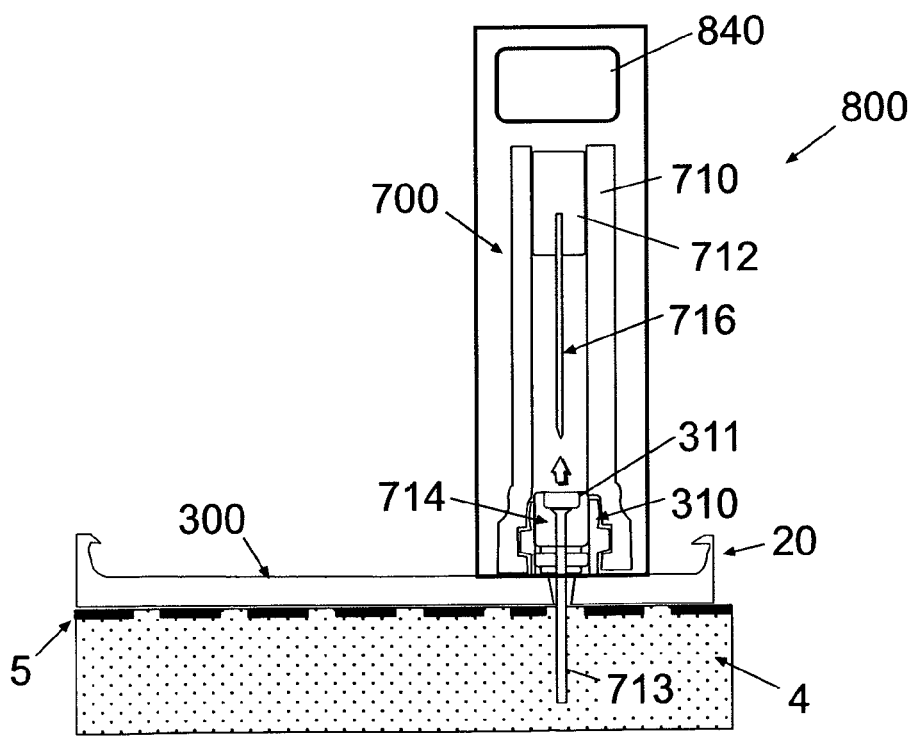

FIG. 9d shows how the penetrating member (716) is being retracted back into the protector (710), according to some embodiments of the present invention. Once the cannula (713) and the penetrating member (716) are inserted, the cannula hub (714) remains connected to the well (310), and the cannula (713) remains in the subcutaneous tissue (4). Retraction of the penetrating member (716) may be carried out manually or automatically by the inserter's displacement mechanism (840). Such retraction of the penetrating member (716) is performed in a similar fashion described above. Once the penetrating member is retracted back into the protector (710), the inserter (800) can be removed, as shown in FIG. 9e.

Figure 9E:
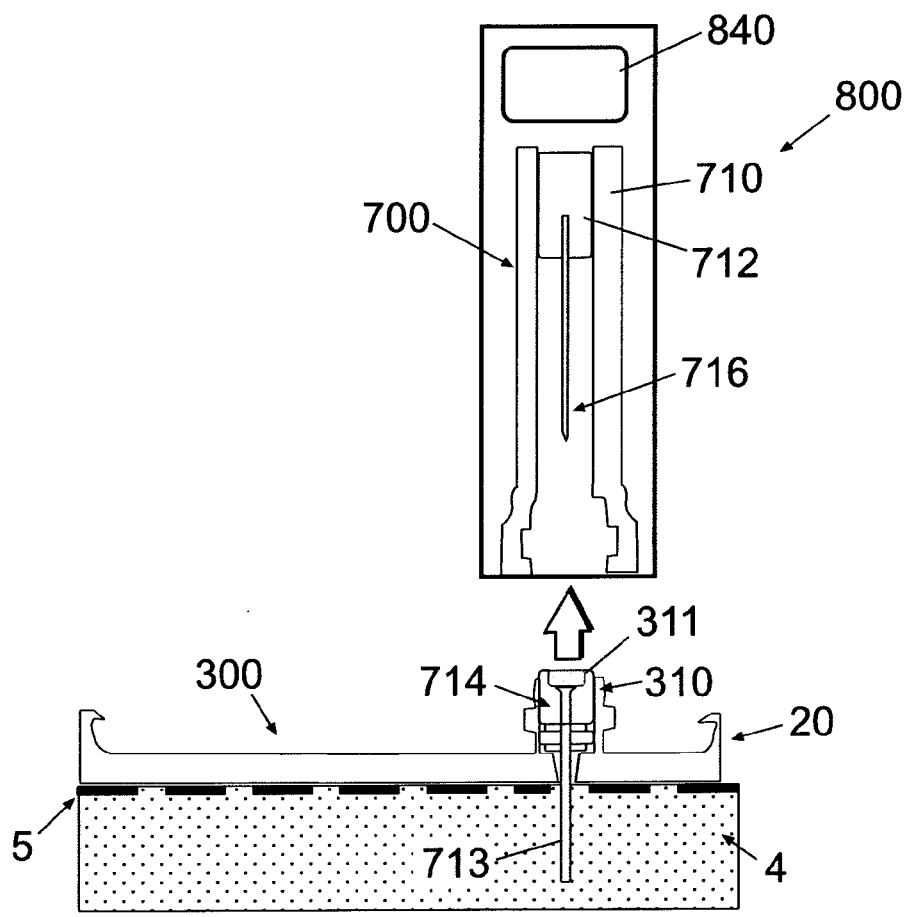

FIG. 9e shows disconnection of the inserter (800) from the cradle unit (20). The protector (710), which still contains the penetrating member (716), is then unloaded from the inserter (800) and can be discarded. The inserter (800) can otherwise be disconnected from the cradle unit (20) after the cannula (713) insertion while the penetrating member (716) remains inside the body. In this case, the user may manually remove the penetrating member (716) from the body by holding the penetrating member's grip portion (712) with his/her fingers and pulling away from the skin (5).

Figure 9F:
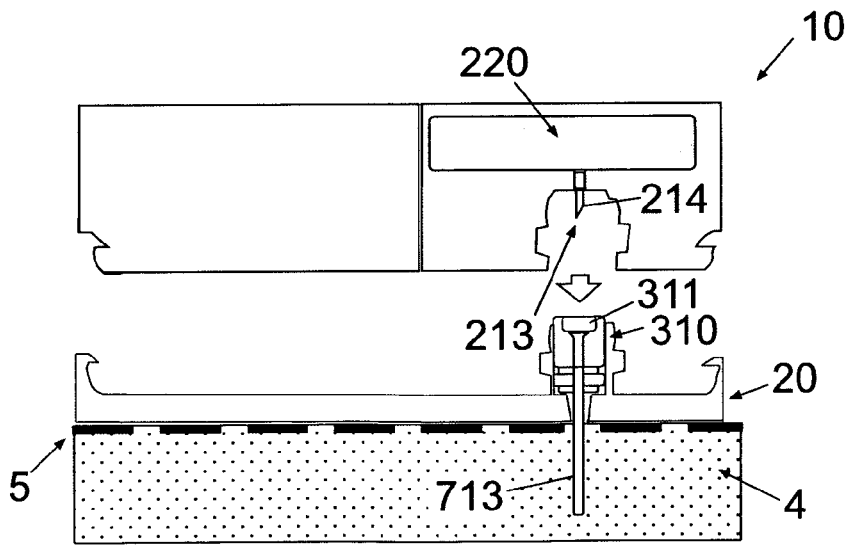

FIG. 9f shows the exemplary two-part dispensing patch unit (10) prior to its connection to the cradle unit (20), according to some embodiments of the present invention. In some embodiments, the dispensing patch unit (10) includes a fluid reservoir (220), an outlet port (213), and a connecting lumen (214) that maintains fluid communication between the reservoir (220) and the outlet port (213). Upon connection of the dispensing patch unit (10) to the cradle unit (20), the connecting lumen (214) pierces the septum (311), which seals the upper opening of the cannula (713), thus allowing fluid delivery via the cannula (713) to the subcutaneous tissue (4). The outlet port (213) allows repetitive connection and disconnection of the dispensing patch unit (10) to and from the cradle unit (20).

Figure 9G:
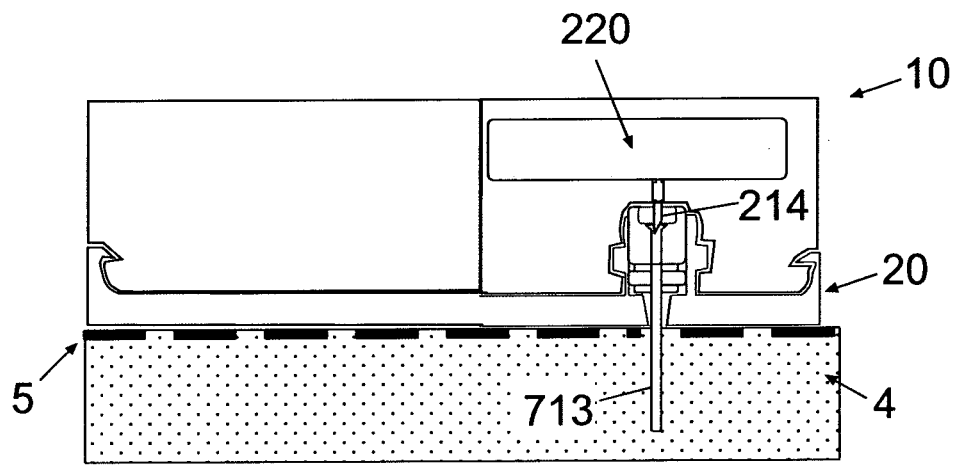

FIG. 9g shows the two-part dispensing patch unit (10) after it has been connected to the cradle unit (20). In some embodiments, the cannula (713) can include a sensor for monitoring a bodily analyte (e.g., glucose). Fluid delivery may be adjusted according to sensor inputs (in a semi- or fully-closed-loop mode). In some embodiments, the dispending patch unit (10) includes both the cannula (713) for drug delivery and the sensor (not shown) for analyte sensing, as disclosed in co-owned, co-pending International Patent Application No. PCT/IL07/000163 and U.S. patent application Ser. No. 11/706,606, both filed Feb. 7, 2007, claiming priority to U.S. Provisional Patent Application No. 60/773,842, filed Feb. 15, 2006, and entitled "An Analyte Sensing and Drug Dispensing System", and in International Patent Application No. PCT/US08/62928 and U.S. patent application Ser. No. 12/116,546 filed May 7, 2008, and claiming priority to U.S. Provisional Patent Application No. 60/928,054, entitled "A Reciprocating System for Monitoring Analyte Concentrations and/or Dispensing Fluids into a Body", and filed May 7, 2007, the disclosures of which are incorporated herein by reference in their entireties.

Hypodermic cannula insertion is accompanied by pain induced by skin piercing. The pain can be reduced using various means, including, for example, applying pressure to the skin in the vicinity of the cannula insertion site or cooling the skin surrounding the insertion site, prior to and/or during the insertion process.

Figure 10A:
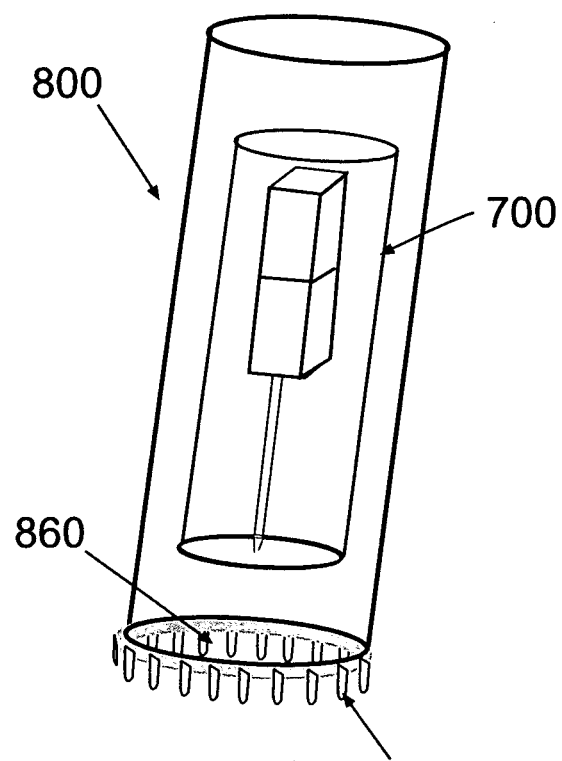
FIGS. 10a-b schematically show an exemplary inserter (illustrated in FIG. 10a) and an exemplary cannula cartridge unit (illustrated in FIG. 10b) provided with an array of protrusions, according to some embodiments of the present invention.

FIGS. 10a-e illustrate exemplary pain alleviating means and devices for reducing pain associated with skin piercing by the penetrating member and the cannula/sensor (not shown), according to some embodiments of the present invention. FIG. 10a shows the inserter (800) loaded with a cannula cartridge unit (700) and provided with an array of protrusions (801) disposed on a perimeter of an open bottom end (860) of the inserter (800). The protrusions (801) are configured to relieve pain associated with the skin piercing by applying pressure to the skin of the user in the vicinity of the insertion site.

Figure 10B:
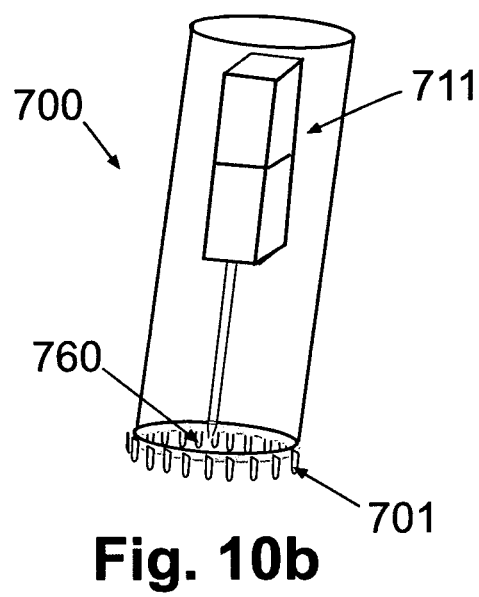

FIG. 10b shows the exemplary cannula cartridge unit (700) provided with an array of protrusions (701), according to some embodiments the present invention. The unit (700) includes an open bottom end (760). The protrusions (701) are disposed around the perimeter of the open bottom end (760). The protrusions can be either blunt or sharp. If blunt protrusions are employed, the protrusions can be fabricated of plastic. In some embodiments, the bottom end (760) and/or (860) includes between 5 to 50 protrusions spread out around the perimeter of bottom end of the inserter (as shown in FIG. 10a) and/or the cannula cartridge unit (as shown in FIG. 10b). In some embodiments, the diameter of the open bottom end of either the inserter and/or the cannula cartridge unit are less than or equal to 3 cm. The dimensions of the blunt protrusions can be as follows: length—between 1 mm and 5 mm, diameter—between 200 µm and 2000 µm, and preferably between 500 µm and 1500 µm. In the case when sharp protrusions (i.e., needles) are employed, the needles can be fabricated of metal, e.g., stainless steel, and there can be between 50 and 500 needles spread around the bottom end of either the inserter and/or the cannula cartridge unit. The dimensions of the needles can be as follows: length—between 1 mm and 5 mm, diameter—between 50 µm and 200µm. In alternate embodiments, combinations of blunt protrusions and sharp needles can be used.

Figure 10C:
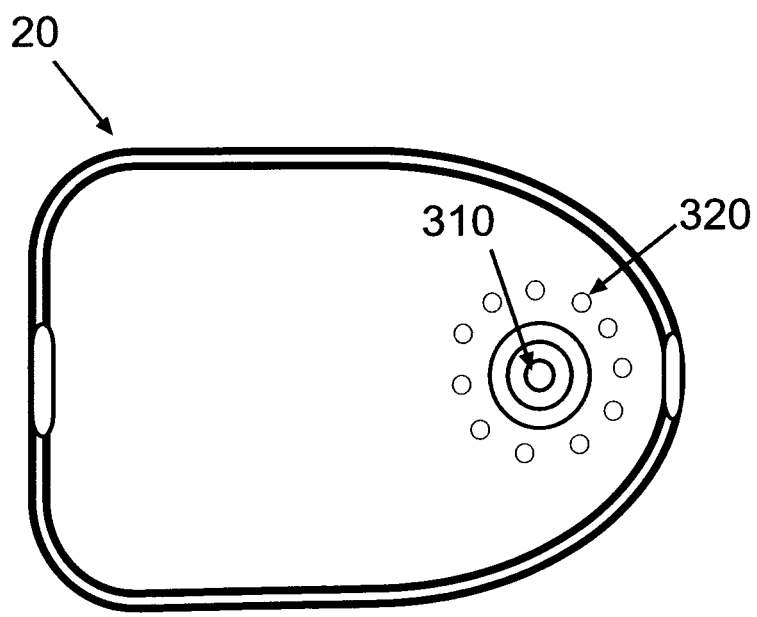
FIGS. 10c-e are upper views of exemplary cradle unit (illustrated in FIG. 10c), well assembly (illustrated in FIG. 10d) and infusion set (illustrated in FIG. 10e) provided with pores, according to some embodiments of the present invention.
Figure 10D:
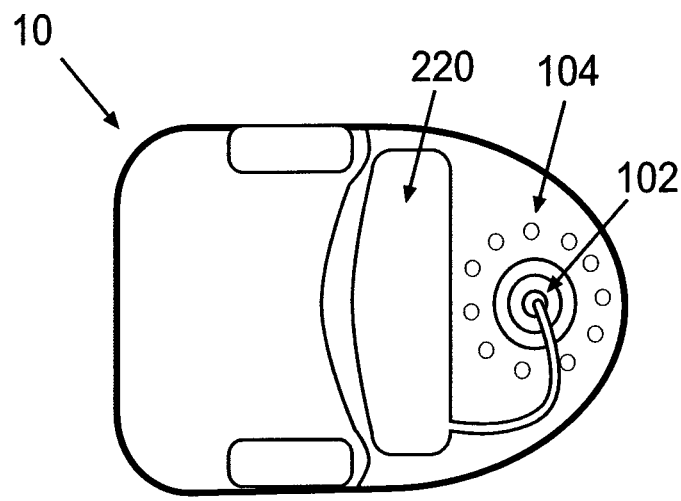
Figure 10E:
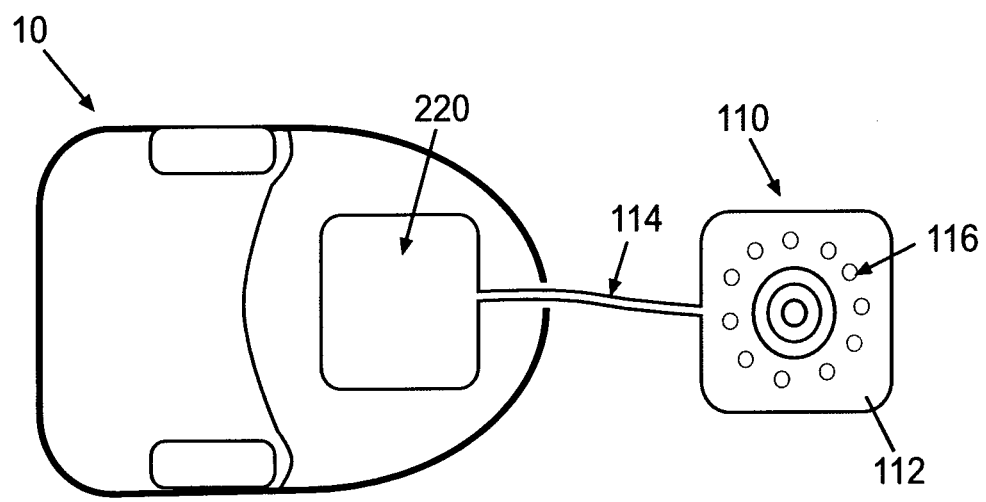

The inserter (800) and the cannula cartridge unit (700) may be used in conjunction with each other or separately. For example, the cannula cartridge unit (700) provided with protrusions (701) may be used as a stand-alone item during manual cannula insertion. Alternatively, the inserter (800) provided with protrusions (801) can be loaded with the cannula cartridge unit (700) (not having the protrusions (701)), or it can be used without the cannula cartridge unit (700), in which case the penetrating cartridge (711) will be contained within the inserter (800) itself FIG. 10c is an upper view of the cradle unit (20) provided with pores/openings (320) surrounding the well (310), according to some embodiments of the present invention. The pores (320) are configured and dimensioned so that the inserter's protrusions and/or the cannula cartridge unit's protrusions can penetrate the pores (320) upon connection of the inserter and/or cannula cartridge unit to the cradle unit (20). Prior to insertion of the cannula, the user applies force onto the inserter and/or cannula cartridge unit, which in turn, apply pressure onto the skin surrounding the well (310) underneath the cradle unit (20). This reduces the pain sensation associated with skin piercing during cannula insertion. The inserter and/or cannula cartridge unit can be connected to the well assembly (102) of the dispensing patch unit (10) which is provided with pores (104) surrounding its opening, as shown in FIG. 10d, or to an infusion set (110), which is provided with pores (116) surrounding its hub's (112) opening, as shown in FIG. 10e. When the inserter provided with protrusions is used in conjunction with the cannula cartridge unit provided with protrusions, the cradle unit, the well assembly, and the infusion set can be provided with two coaxial sets of pores.

Figure 11A:
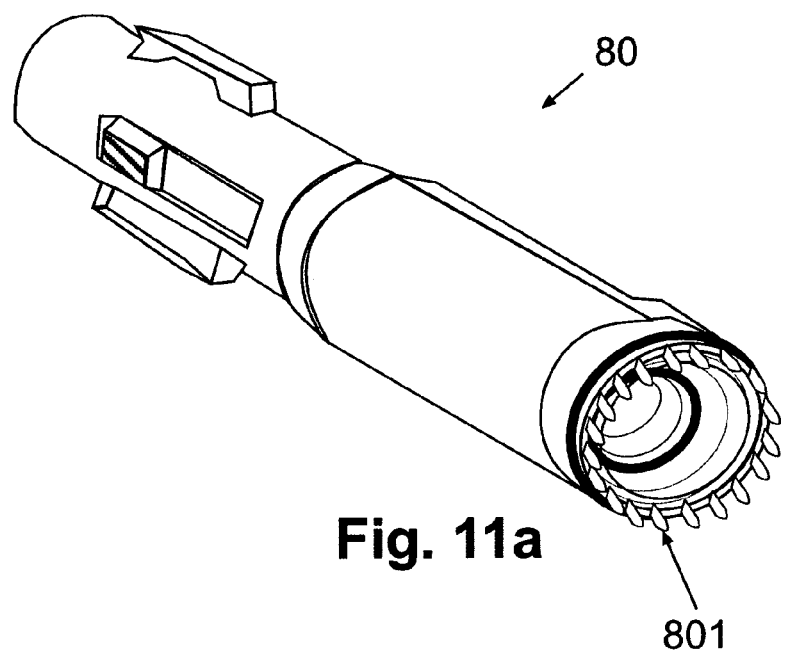
FIGS. 11a-c show an exemplary inserter provided with an array of protrusions (illustrated in FIG. 11a), a cradle unit provided with pores surrounding its well (illustrated in FIG. 11b), and their connection (illustrated in FIG. 11c), according to some embodiments of the present invention.
Figure 19A:
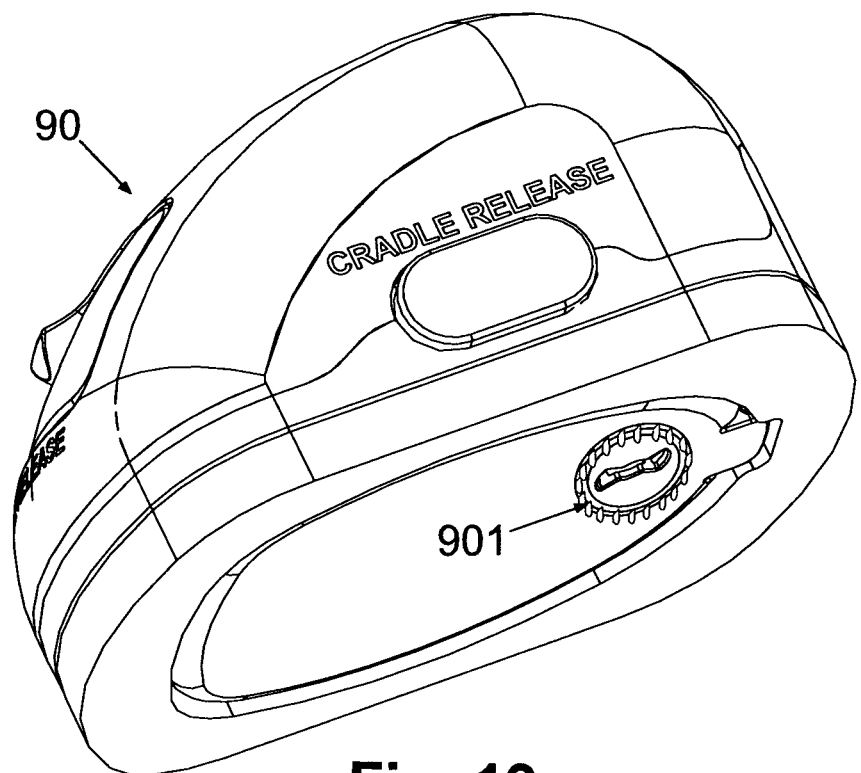
FIG. 19a-b show an exemplary mouse-like inserter provided with an array of protrusions, according to some embodiments of the present invention.
Figure 19B:
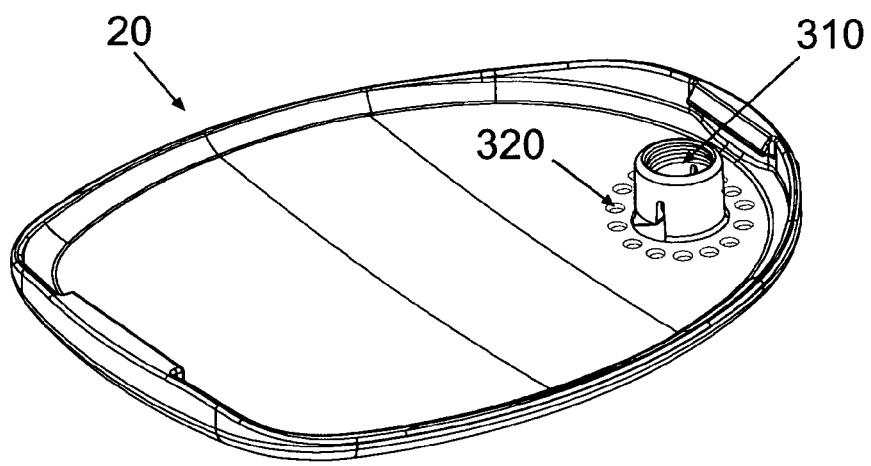

FIG. 11a shows the exemplary pen-like inserter (80) provided with an array of protrusions (801) surrounding its bottom opening, according to some embodiments of the present invention. As can be understood by one skilled in the art, a mouse-like inserter can be used with an array of protrusions, as is shown in FIGS. 19a-b.

Figure 11B:
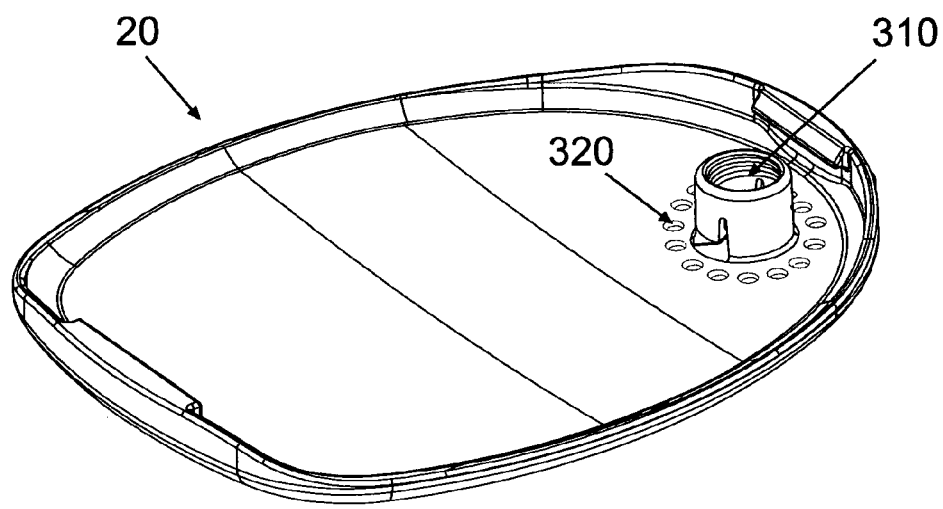

FIG. 11b shows the exemplary cradle unit (20) having pores (320) disposed around the well (310), according to some embodiments of the present invention. The pores (320) are configured to accommodate insertion of the protrusions (801) of the inserter (80) shown in FIG. 11a.

Figure 11C:
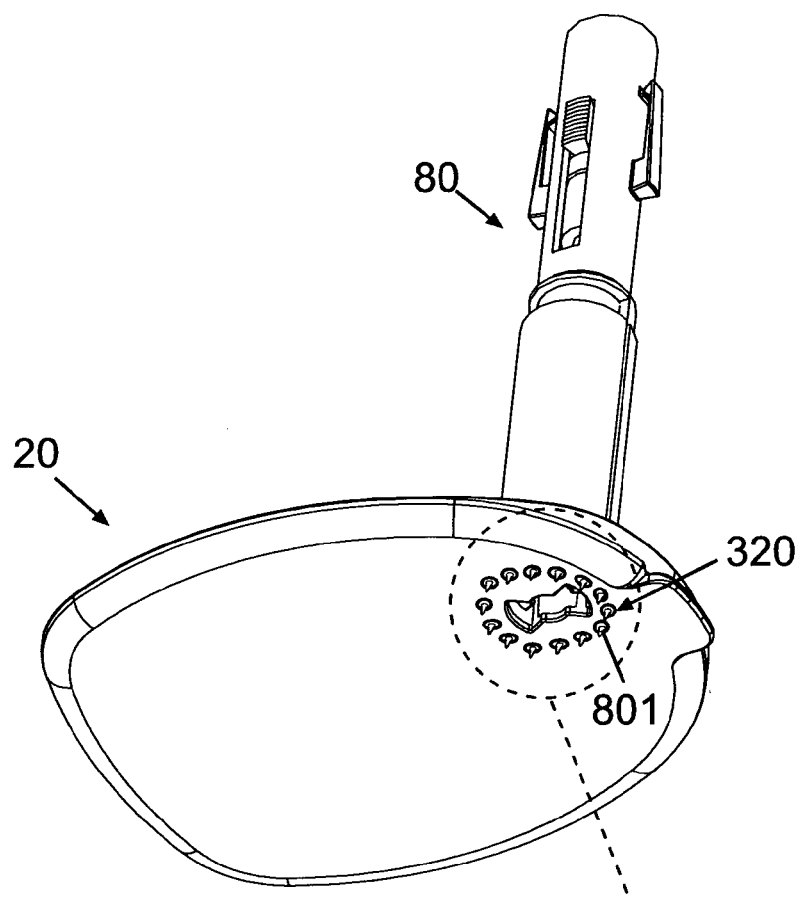
Figure 11C:
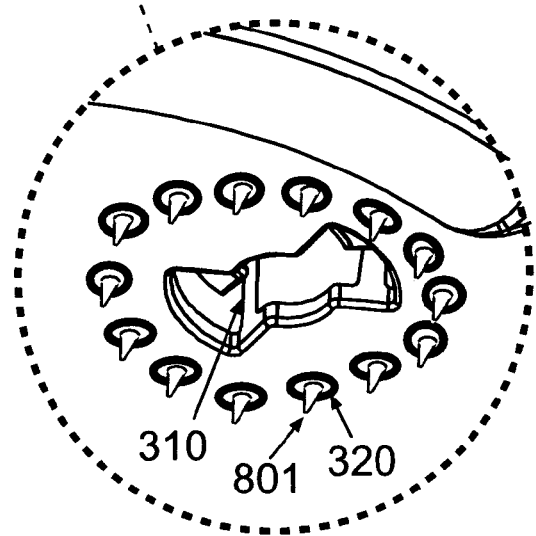
Figure 11D:
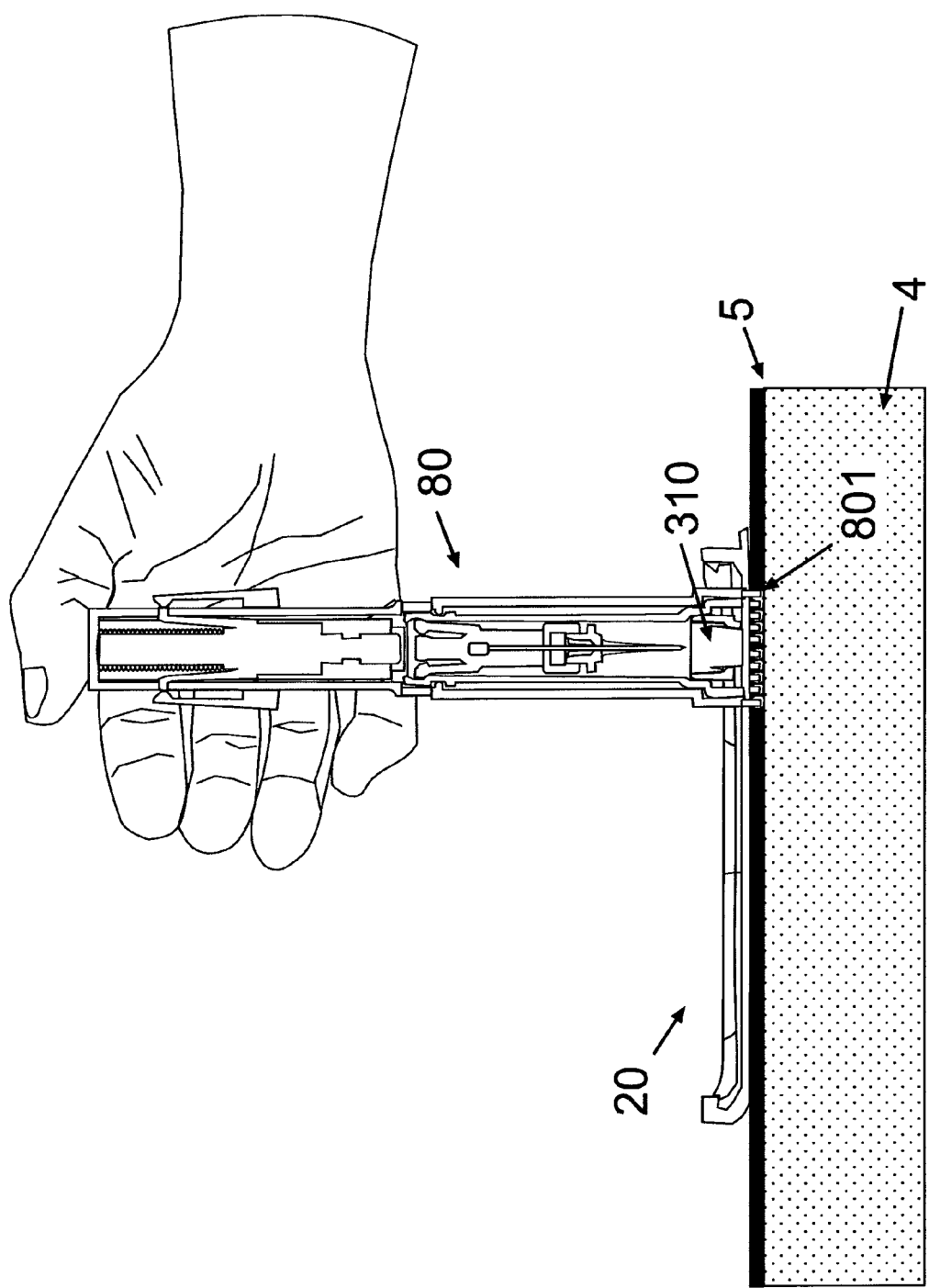
FIGS. 11d-e are cross-sectional views of the inserter shown in FIG. 11a connected to the cradle unit shown FIG. 11b, and a process of inserting the cannula with the aid of the inserter, according to some embodiments of the present invention.

FIG. 11c shows the inserter (80) shown in FIG. 11a and the cradle unit (20) shown in FIG. 11b connected to each other. The inserter's (80) protrusions (801) are aligned with the pores (320) made in the cradle unit (20). FIG. 11d is a cross-sectional view of the inserter (80) connected to the cradle unit (20) adhered to the skin. Prior to insertion of the cannula, the user applies force onto the inserter (80), which in turn, applies pressure onto the skin underneath the cradle unit (20) surrounding a bottom of the well (310) via the protrusions (801). The protrusions (801) protrude through the pores (320) in the cradle unit (20). By virtue of applying pressure via the array of protrusions, it is possible to reduce the pain sensation associated with skin piercing during cannula insertion.

Figure 11E:
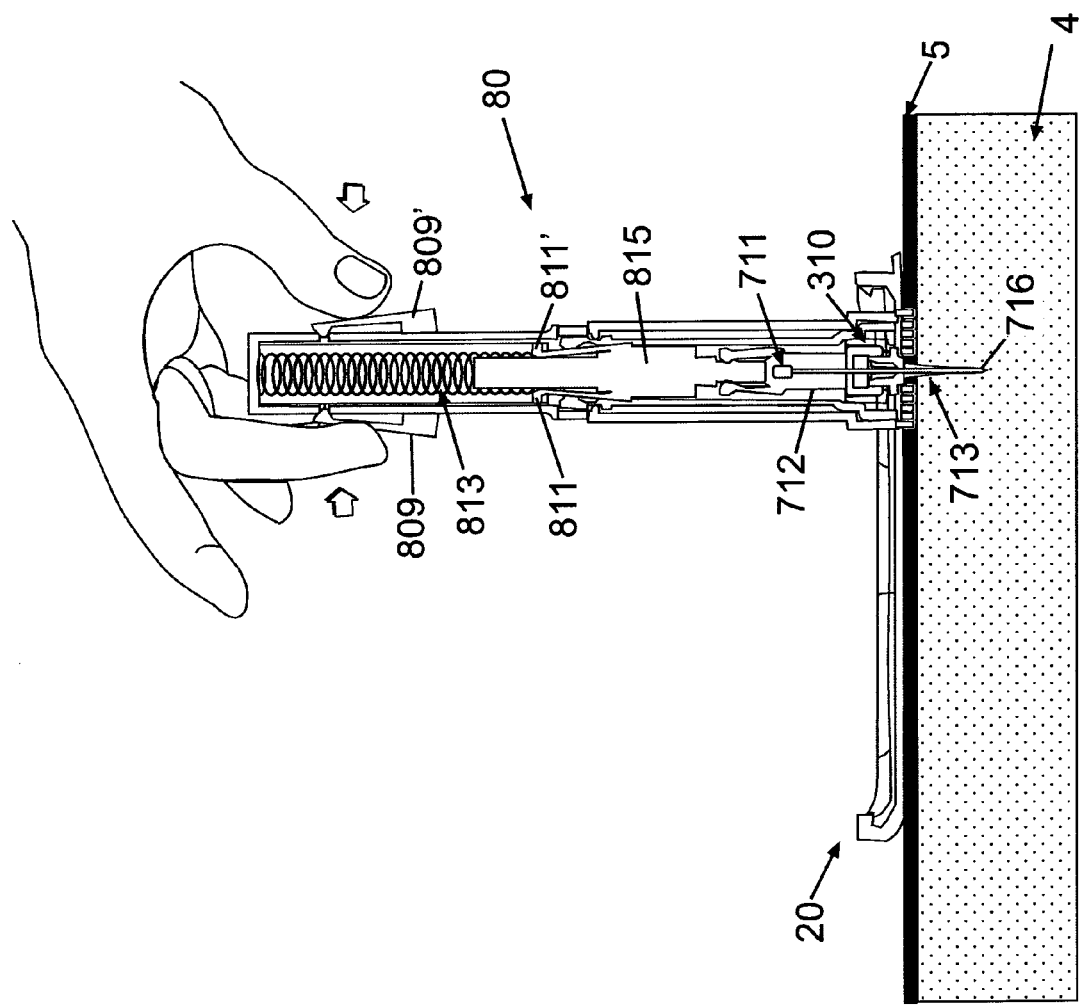

FIG. 11e shows the insertion of the cannula (713) with the sharp penetrating member (716) into the subcutaneous tissue (4). Here, the user initiates the insertion process by simultaneously pressing two lateral triggers (809), (809') disposed on the inserter housing. The triggers (809), (809') release a spring (813) from its loaded state. The spring (813) is attached to a dedicated rod (815) which is then shot downwardly. The rod (815) pushes the penetrating cartridge towards the well (310). This insertion process is disclosed in co-owned, co-pending U.S. patent application Ser. No. 12/215,219 and International Patent Application No. PCT/IL08/000859, claiming priority to U.S. Provisional Patent Application No. 60/937,155, entitled "Protector for Cannula and Penetrating Member Insertable in the Body of a Patient", U.S. Provisional Patent Application No. 60/937,214, entitled "Insertion Device for Inserting a Cannula into a Body", and U.S. Provisional Patent Application No. 60/937,163, entitled "Devices and Methods for Pain Reduction", all filed Jun. 25, 2007, the disclosures of which are incorporated herein by reference in their entireties.

Figure 12A:
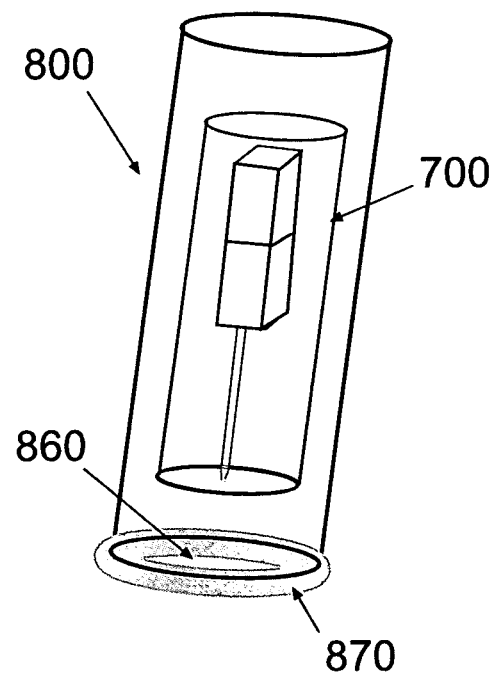
FIGS. 12a-b schematically show an exemplary inserter (illustrated in FIG. 12a) and an exemplary cannula cartridge unit (illustrated in FIG. 12b) provided with an annular cooling plate, according to some embodiments of the present invention.
Figure 12B:
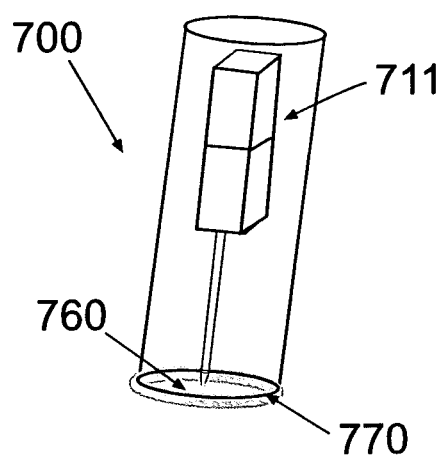

FIG. 12a schematically shows the inserter (800) having an annular cooling plate (870), a pain reduction means, which may deployed around the opened bottom end (860) of the inserter, according to some embodiments of the present invention. FIG. 12b schematically shows the cannula cartridge unit (700) provided with an annular cooling plate (770) surrounding its opened bottom end (760), according to some embodiments of the present invention. As can be understood by one skilled in the art, the shape of the cooling plates (870) and (770) is not limited to an annular shape. In some embodiments, the cooling plate is shaped to fit around the inserter's opened bottom end (860) and/or cannula cartridge unit's opened bottom end (760). The inserter (800) and the cannula cartridge unit (700) can be used in conjunction with each other or separately, as explained above with reference to FIGS. 10a-b. Prior to usage, the inserter (800) and/or the cannula cartridge unit (700) is stored in a cooling facility (i.e., refrigerator, freezer, etc., not shown) in order to keep the cooling plates (870), (770) cold. The cooling plates (870), (770) are fabricated from a material having high thermal conductivity and high thermal capacity, e.g., copper, aluminum, etc. The cooling plates (870), (770) can be an integral part of the inserter (800) and/or the cannula cartridge unit (700), respectively. In some embodiments, they can be separate items which are manually attached to the inserter (800) and/or cannula cartridge unit (700) before usage, respectively, for example by means of magnets (not shown) provided around the inserter's opened bottom end (860) and/or the cannula cartridge unit's opened bottom end (760). In this case, only the cooling plates (870), (770) can be stored in a cooling facility prior to usage of the inserter (800) and/or cannula cartridge unit (700), respectively. As stated above, the cooling plates (870) and (770) are configured to cool the skin around the insertion site and thereby relieve pain and discomfort associated with skin-piercing.

Figure 12C:
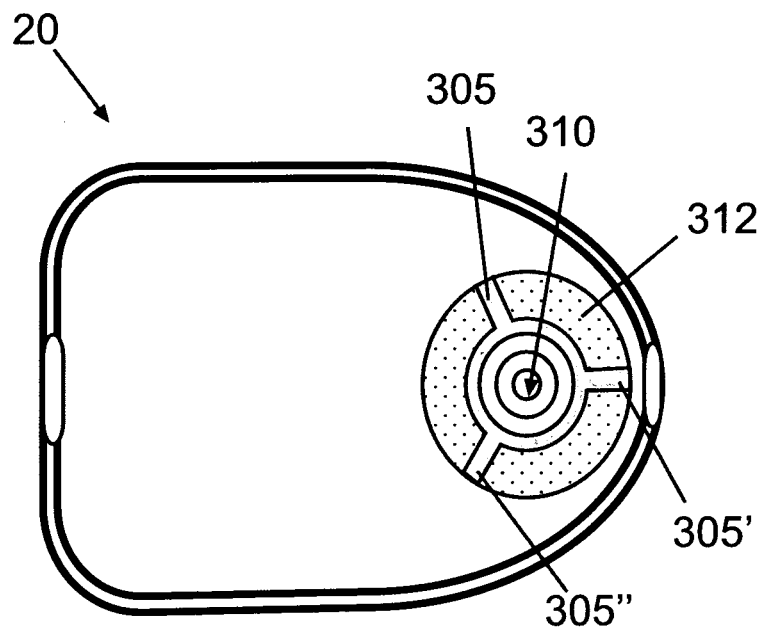
FIG. 12c is an upper view of an exemplary cradle unit provided with arcuate windows surrounding its well, according to some embodiments of the present invention.
Figure 13A:
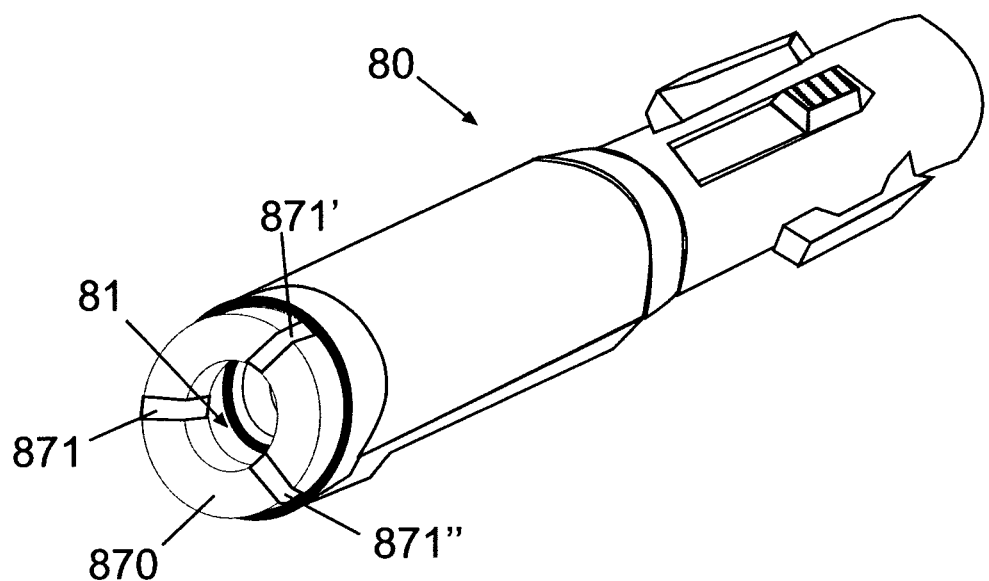
FIGS. 13a-d show exemplary inserter provided with an annular cooling plate (illustrated in FIG. 13a), a cradle unit provided with arcuate windows (illustrated in FIG. 13b), and connection of the cradle unit and the inserter (illustrated in FIGS. 13c-d), according to some embodiments of the present invention.

FIG. 12c is an upper view of the cradle unit (20) having arcuate windows (312) surrounding its well (310), according to some embodiments of the present invention. The windows (312) can be configured such that the inserter's and/or cannula cartridge unit's cooling plate (not shown) can fit within the windows (312) upon connection to the cradle unit (20) and maintain physical contact with the user's skin. The cooling plate thus cools the area surrounding the insertion site, and as a result the pain sensation associated with skin piercing during cannula insertion is reduced. In order to maintain connection between the well (310) and the cradle base (300), connectors or protrusions or "bridges" (305), (305'), and (305") are provided between the windows (312). In this embodiment, the cooling plate has grooves or depressions (871), (871'), and (871"), which divide the cooling plate (870) to sectors, as shown in FIG. 13a. The depressions (871), (871'), and (871") are configured to fit over the respective "bridges" (305), (305'), (305"). The "bridges" (305), (305'), (305") provide a secure connection between the cradle unit (20) and the inserter (80), thereby assuring that the cooling effects of the cooling plate are properly maintained throughout the insertion. Similarly, a dispensing patch unit's well assembly may be provided with a groove surrounding its opening, or an infusion set may be provided with a groove surrounding its hub's opening.

Figure 13B:
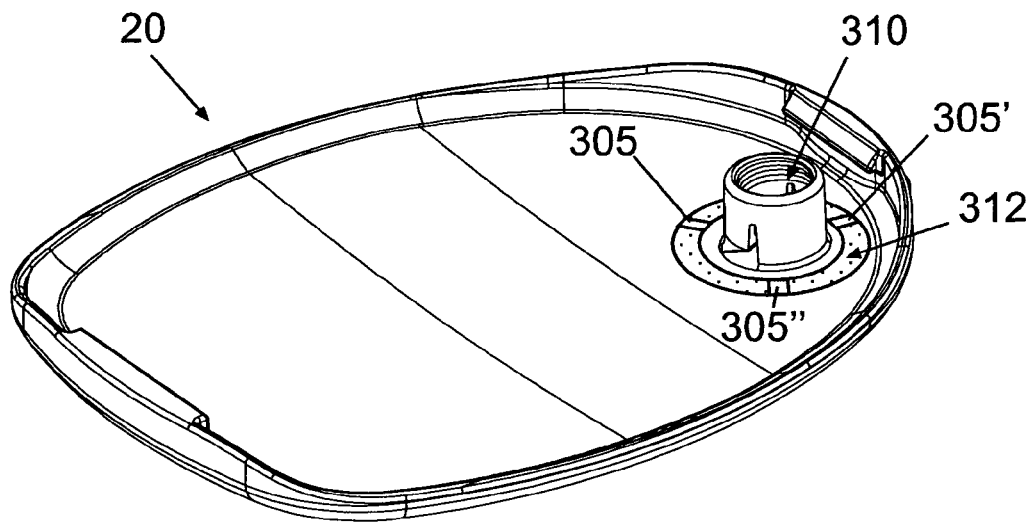
Figure 13C:
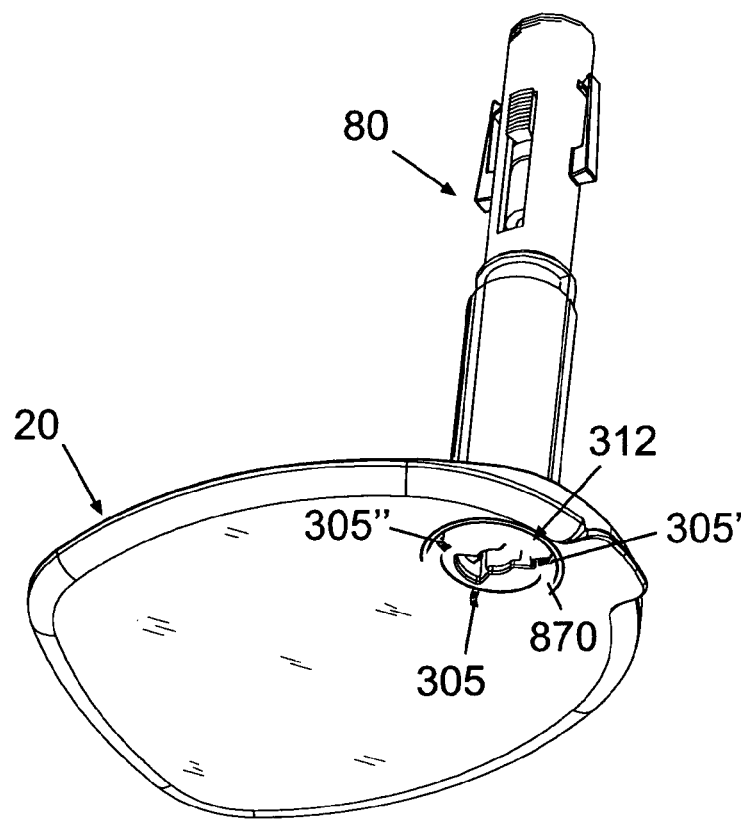

FIG. 13a shows the exemplary pen-like inserter (80) having an annular cooling plate (870) surrounding its opened bottom end (81) and having grooves or depressions (871), (871'), and (871"), according to some embodiments of the present invention. As can be understood by one skilled in the art, the bottom end (81) can include any number of depressions. FIG. 13b shows the exemplary cradle unit (20) having an arcuate windows (312) surrounding its well (310) and defined by "bridges" (305), (305'), (305") to maintain connection between the well (310) and the cradle base (300). FIG. 13c shows the inserter (80) shown in FIG. 13a and the cradle unit (20) shown in FIG. 13b connected to each other. As shown, the inserter's cooling plate (870) fits over the cradle unit's arcuate windows (312). In some embodiments, to properly secure the inserter (80) to the cradle unit (20), the user aligns the "bridges" (305), (305') and (305") with the grooves (871), (871') and (871"), as well as places the inserter (80) over the well (310), and then secures the inserter (80). Once the inserter (80) is secured, the user can begin skin piercing procedure, while the cooling plate (870) cools the user's skin to alleviate pain.

Figure 13D:
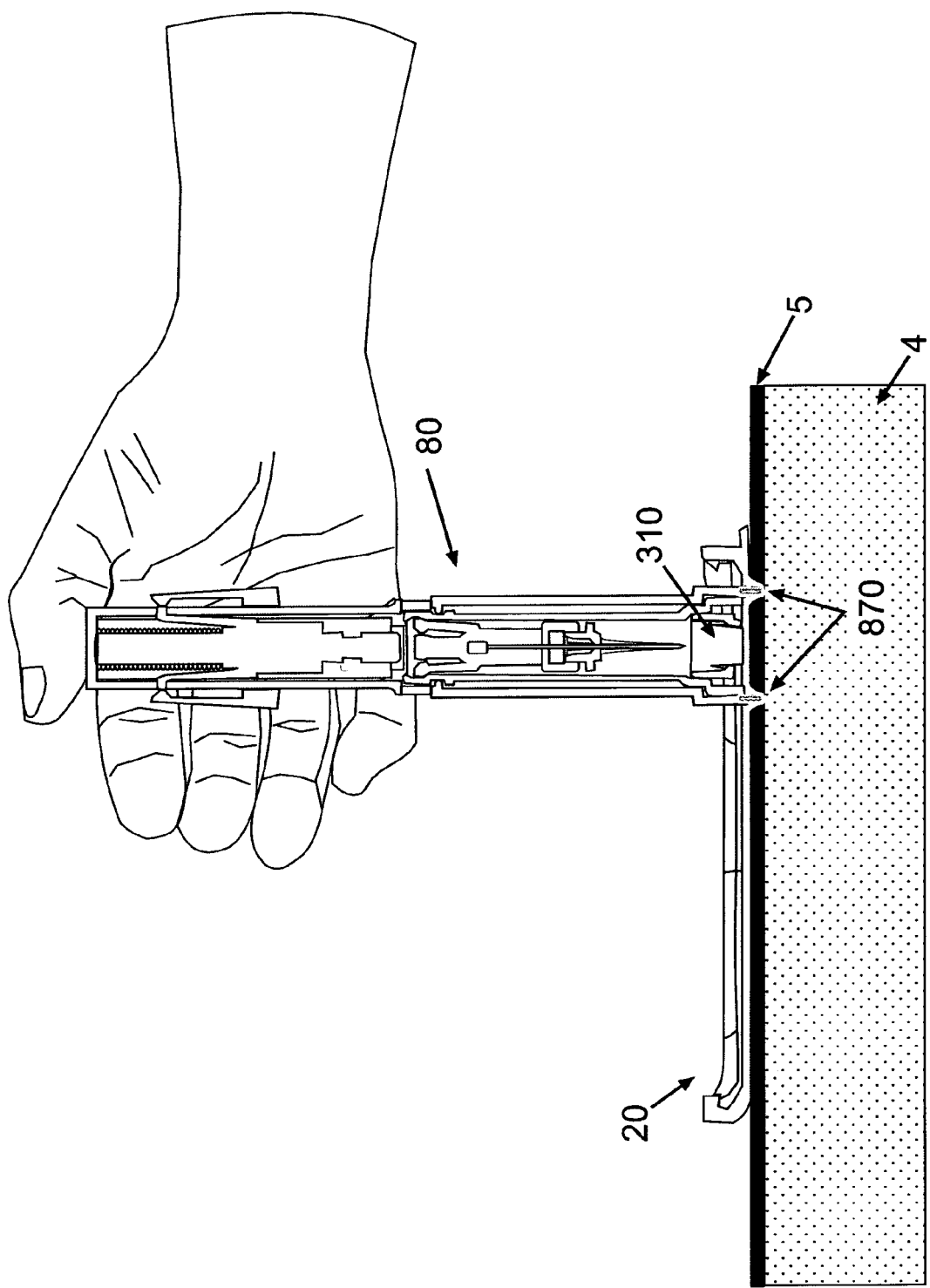

FIG. 13d is a cross-sectional view of the inserter (80) connected to a skin adhered cradle unit (20). The cooling plate (870) comes in contact with the skin surrounding the well (310) as the plate protrudes through the windows (312) towards the skin. The cooling plate (870) cools the area surrounding the insertion site. As a result, the pain sensation associated with skin piercing during cannula insertion is reduced. The cannula insertion process can be carried out similar to the one described above in reference to FIG. 11e.

Figure 14A:
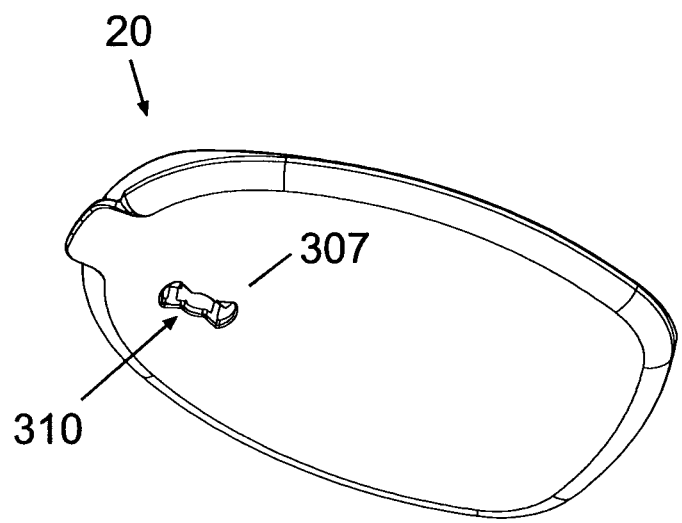
FIGS. 14a-b show an exemplary cradle unit provided with a cooling plate, according to some embodiments of the present invention.
Figure 14B:
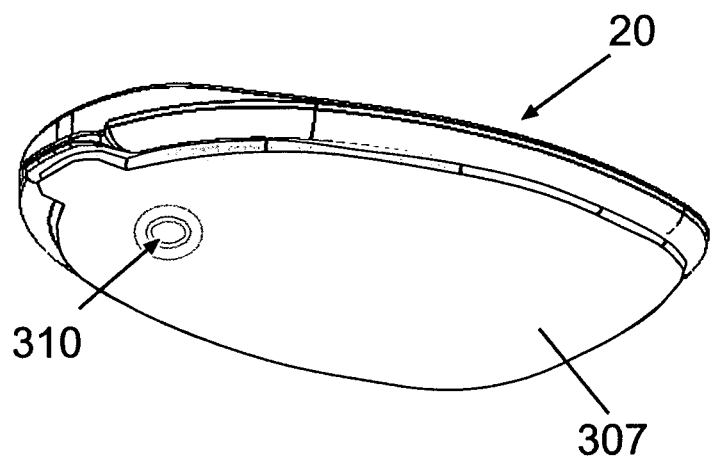

FIGS. 14a-b shows another exemplary embodiment of a skin cooling means. In this embodiment, the cradle unit (20) includes a cooling plate (307). The cooling plate (307) can be configured as a ring surrounding the bottom portion of the well (310), as shown in FIG. 14a. Alternatively, the cooling plate (307) can be configured as a sheet covering the bottom surface of the cradle unit (200) either partially or entirely, as shown in FIG. 14b. In some embodiments, the cooling plate (307) is an integral part of the cradle unit (20). The cradle unit (20) can be stored in a cooling facility (e.g., refrigerator, etc.) prior to adherence to the skin so that the cooling plate (307) is cooled. In other embodiments, the cooling plate (307) is a separate item, which can be stored in a cooling facility (e.g., refrigerator, etc.) and then manually attached to the cradle unit (20) before attaching the cradle unit (20) to the skin. The cooling plate (307) can be fabricated from material(s) having high thermal conductivity and high thermal capacity, e.g., copper, aluminum, etc. Upon adherence to the user's skin, the cooling plate (307) cools the skin surrounding the insertion site, thereby reducing the pain sensation associated with skin piercing during insertion of the cannula. Similarly, an infusion set (not shown) may be provided with a cooling plate either surrounding its hub's bottom opening, or covering its bottom surface entirely.

A "regular" inserter (not shown) and cannula cartridge unit (not shown) can be used, i.e., an inserter and cannula cartridge unit not having any special features related to pain reduction, and the cannula insertion process which follows the connection of the inserter to the cradle unit may be carried out as discussed in co-owned, co-pending U.S. patent application Ser. No. 12/215,219 and International Patent Application No. PCT/IL08/000859, claiming priority to U.S. Provisional Patent Application No. 60/937,155, entitled "Protector for Cannula and Penetrating Member Insertable in the Body of a Patient", U.S. Provisional Patent Application No. 60/937,214, entitled "Insertion Device for Inserting a Cannula into a Body", and U.S. Provisional Patent Application No. 60/937,163, entitled "Devices and Methods for Pain Reduction", all filed Jun. 25, 2007, and International Patent Application No. PCT/IL08/000860, and U.S. patent application Ser. No. 12/215,255, claiming priority to U.S. Provisional Patent Application No. 60/937,214, entitled "Insertion Device for Inserting a Cannula into a Body", U.S. Provisional Patent Application No. 60/937,155, entitled "Protector for Cannula and Penetrating Member Insertable in the Body of a Patient", and U.S. Provisional Patent Application No. 60/937,163, entitled "Devices and Methods for Pain Reduction", all filed Jun. 25, 2007, the disclosures of which are incorporated herein by reference in their entireties, the disclosures of which are incorporated herein by reference in their entireties.

Figure 15:
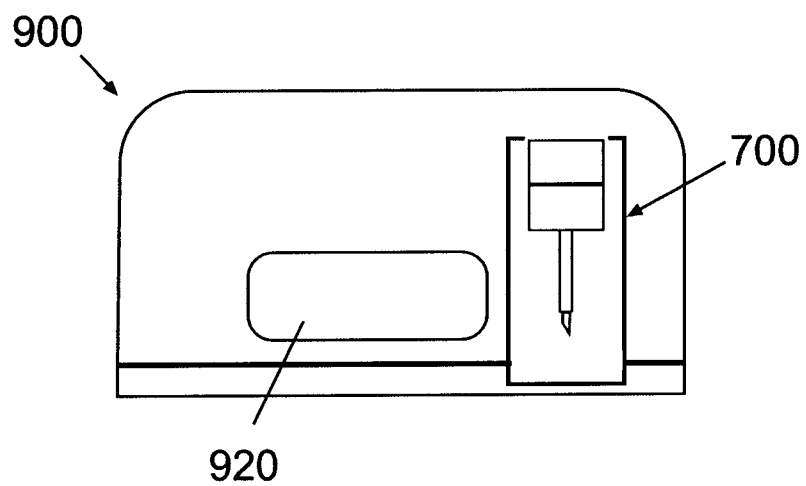
FIG. 15 schematically shows an inserter provided with a cooling mechanism, according to some embodiments of the present invention.

FIG. 15 schematically shows the inserter (900) having a cooling mechanism (920), according to some embodiments of the present invention. The cooling mechanism (920) can be configured as a gas container or a thermoelectric cooler ("TEC") that operates according to the Peltier effect. The Peltier effect is sometimes referred to being a part of a thermoelectric effect, which is the direct conversion of temperature differences to electric voltage and vice versa. To create a thermoelectric effect, a thermoelectric device creates a voltage when there is a different temperature on each side, and when a voltage is applied to it, it creates a temperature difference. This effect can be used to generate electricity, to measure temperature, to cool objects, or to heat them. Because the direction of heating and cooling is determined by the sign of the applied voltage, thermoelectric devices make very convenient temperature controllers. Referring to FIG. 15, a cooling mechanism may be employed in various types of inserters (900), and it may be activated upon connection of the inserter (900) either to the cradle unit, or to the well assembly, or to the infusion set, prior to and/or during cannula insertion.

Figure 16:
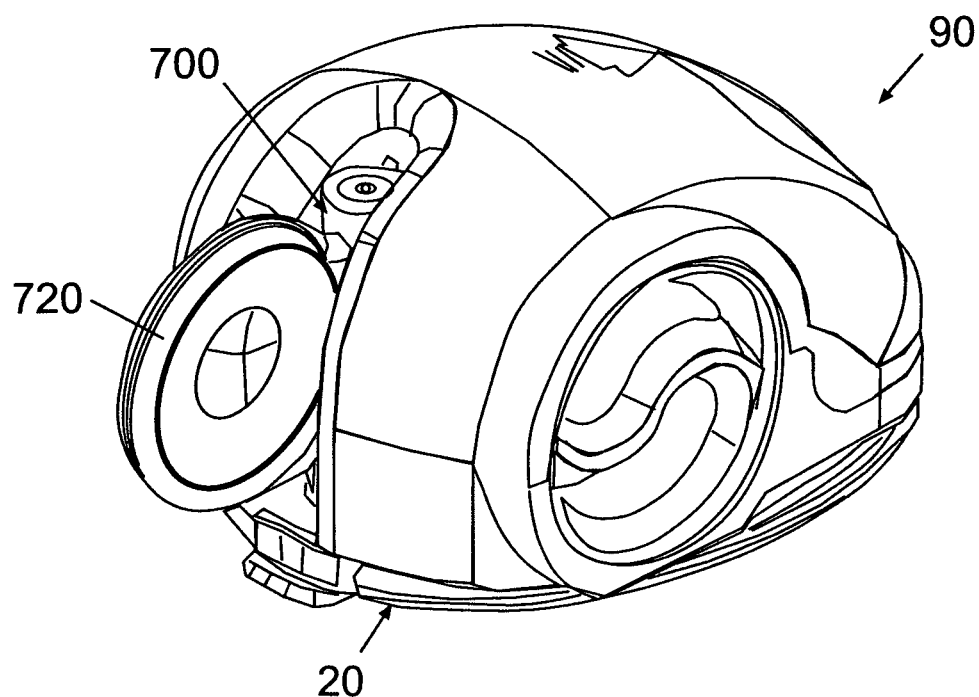
FIG. 16 shows an exemplary inserter fitted with a cooling mechanism, according to some embodiments of the present invention.

FIG. 16 shows an exemplary inserter (90) having a cooling mechanism, according to some embodiments of the present invention. FIG. 16 shows a mouse-like inserter (90) preloaded with the cradle unit (20) and the cannula cartridge unit (700) having a handle (720). The connection of the inserter (90) to the cradle unit (20) and the loading of the cannula cartridge unit (700) into the inserter (90) are discussed in co-owned, co-pending U.S.patent application Ser. No. 12/215,219and International Patent Application No. PCT/IL08/000859, claiming priority to U.S. Provisional Patent Application No. 60/937,155, entitled "Protector for Cannula and Penetrating Member Insertable in the Body of a Patient",U.S. Provisional Patent Application No. 60/937,214, entitled "Insertion Device for Inserting a Cannula into a Body", and U.S. Provisional Patent Application No. 60/937,163, entitled "Devices and Methods for Pain Reduction", all filed Jun. 25, 2007 and Co-owned/co-pending International Patent Application No. PCT/IL08/000860and U.S. patent application Ser. No. 12/215,255, claiming priority to U.S. Provisional Patent Application No. 60/937,214, entitled "Insertion Device for Inserting a Cannula into a Body", U.S. Provisional Patent Application No. 60/937,155, entitled "Protector for Cannula and Penetrating Member Insertable in the Body of a Patient", and U.S. Provisional Patent Application No. 60/937,163, entitled "Devices and Methods for Pain Reduction", the disclosures of which are incorporated herein by reference in their entireties. The inserter's (90) displacement mechanism in this embodiment employs a spring loaded flywheel (not shown).

Figure 17A:
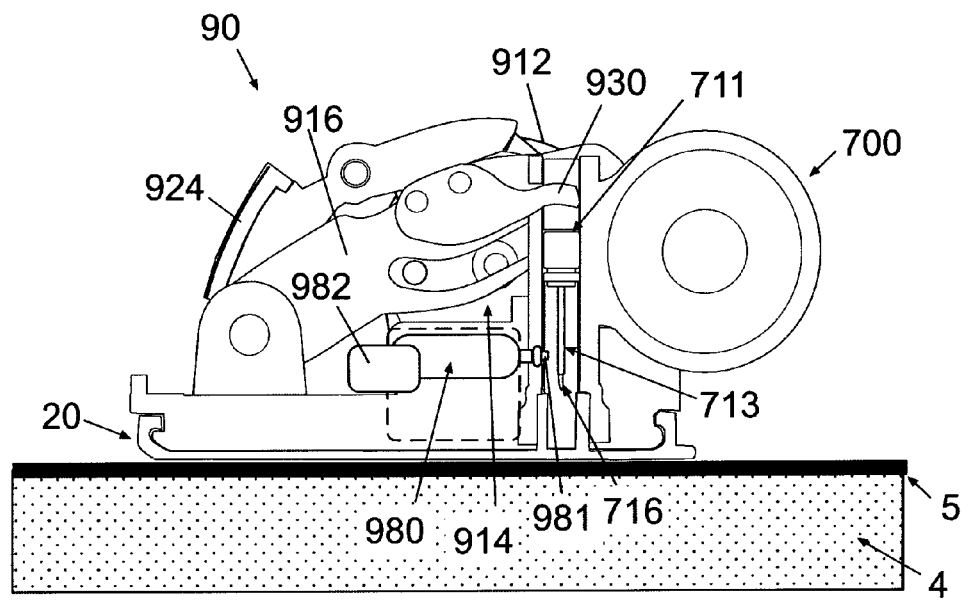
FIGS. 17a-c show an exemplary inserter fitted with a gas container for releasing the cooling gas from the gas container, according to some embodiments of the present invention.

FIG. 17a is a cross-sectional view of the mouse-like inserter (90) having a gas container (980) as a cooling mechanism, according to some embodiments of the present invention. Upon loading the spring, the user attaches the cradle unit (20) to the skin (5) and presses a release button (924). Insertion of the cannula (713) and penetrating member (716)into the body, and retraction of the penetrating member (716) therefrom are carried out automatically by means of a spring loaded flywheel (912) associated to a ratchet crank (914) and at least one dedicated engagement hook (930) which maintains contact with the penetrating cartridge (711) through the protector's (710) at least one longitudinal slit (not shown in FIG. 17*a*). An example of this insertion process is disclosed in co-owned/co-pending International Patent Application No. PCT/IL08/000860 and U.S. patent application Ser. No. 12/215,255 claiming priority to U.S. Provisional Patent Application No.60/937,214, entitled "Insertion Device for Inserting a Cannula into a Body",U.S. Provisional Patent Application No. 60/937,155, entitled "Protector for Cannula and Penetrating Member Insertable in the Body of a Patient", and U.S. Provisional Patent Application No. 60/937,163, entitled "Devices and Methods for Pain Reduction", the disclosures of which are incorporated herein by reference in their entireties.

In some embodiments, the cooling gas container (980) is disposed in the inserter (90) near the loading area of the cannula cartridge unit (700). The cooling gas container (980) is coupled to an actuation mechanism (982) that controls release of the cooling gas into the protector (710). The cooling gas is released from the container (980) via an outlet port (981) of the container (980). The outlet port (981) can be a nozzle that controls release of the gas. The actuation mechanism (982) can be coupled to the displacement mechanism within the inserter (90). Release of the cooling gas from the gas container (980) may begin either prior to initiation of the cannula insertion process using a switching mechanism (not shown) provided in the inserter (90), or upon initiation of the cannula insertion process using the actuation mechanism (982) that opens the gas container's outlet port (981). The actuation mechanism (982) can release gas automatically (e.g., upon release of the cannula), manually by the user, or in any other way. The cooling gas can be released simultaneously with the cannula and/or it can be released prior to the cannula release and/or after cannula release and/or at any other time, as desired. Further, the cooling gas can be substituted with any other substance, e.g., a cooling gel, etc.

Figure 17B:
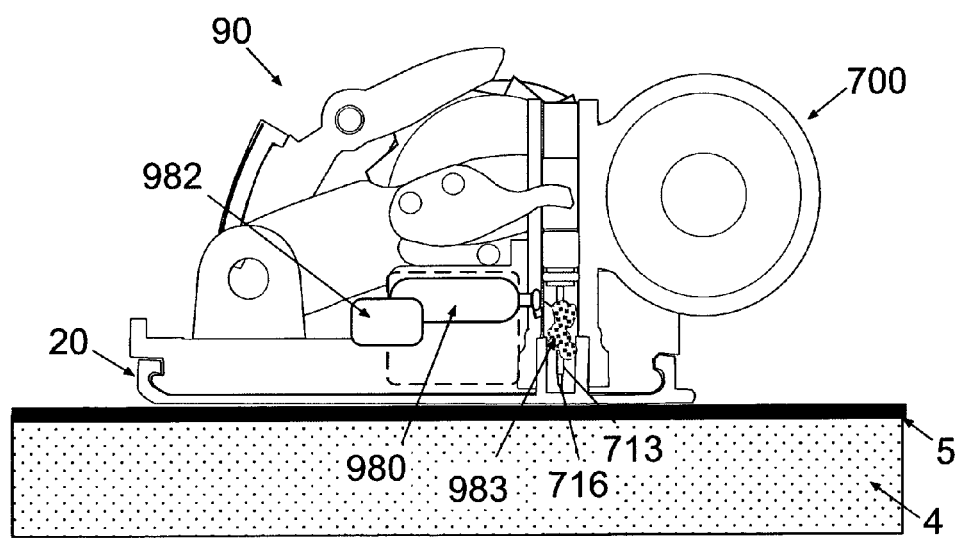
Figure 17C:
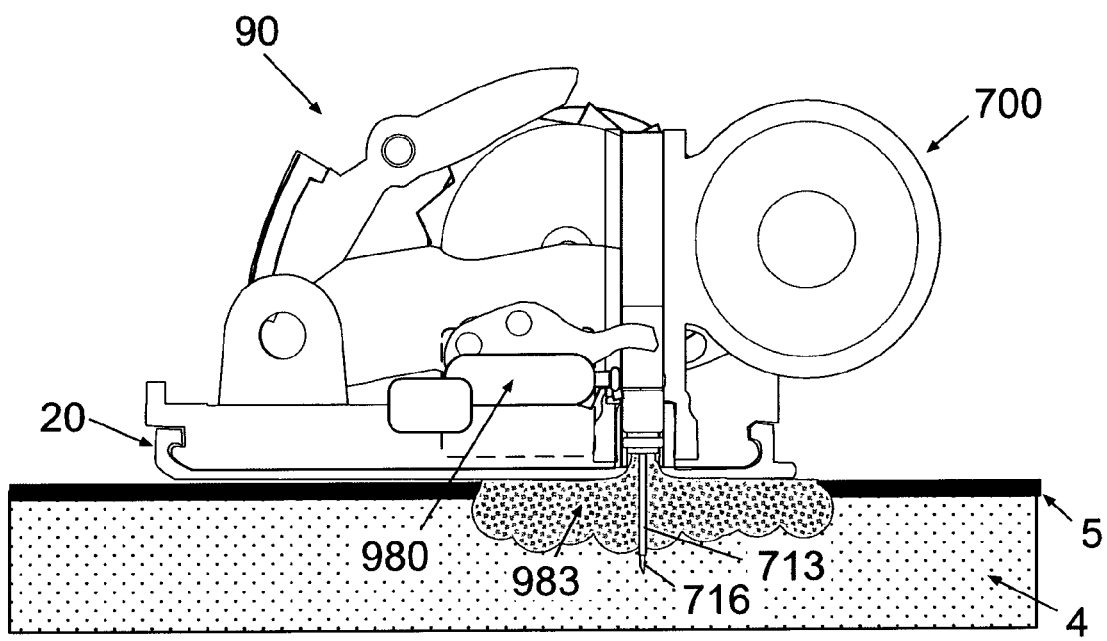

FIGS. 17*b-c* show release of the cooling gas (983) from the gas container (980) and the insertion of the cannula (713) into the subcutaneous tissue (4). In some embodiments, the gas (983) is released inwardly onto the bottom section of the cannula cartridge unit (700), thereby cooling the insertion site prior to skin piercing. The gas container (980) can include enough gas to achieve skin cooling during a single and/or multiple insertion process(es). The container can be either refilled or replaced after each insertion through an opening in the inserter's housing (not shown). The cooling gas lowers the temperature of an area that sufficiently surrounds the insertion site, thereby reducing the feeling of painful effects associated with skin piercing.

FIG. 18*a* is a cross-sectional view of the mouse-like inserter (90) having another exemplary pain reduction means, according to some embodiments of the present invention. In this case, the pain reduction means is a thermoelectric cooler ("TEC") (990), the operation of which is based on the Peltier effect, i.e., on conversion of electric voltage into temperature gradient. The TEC (990) (also shown separately in FIG. 18*b*) includes a cooling plate (991), a heat transfer means (992) and a heat sink (993). The TEC (99) is connected to a DC source (995) provided within the inserter (90).

Figure 18C:
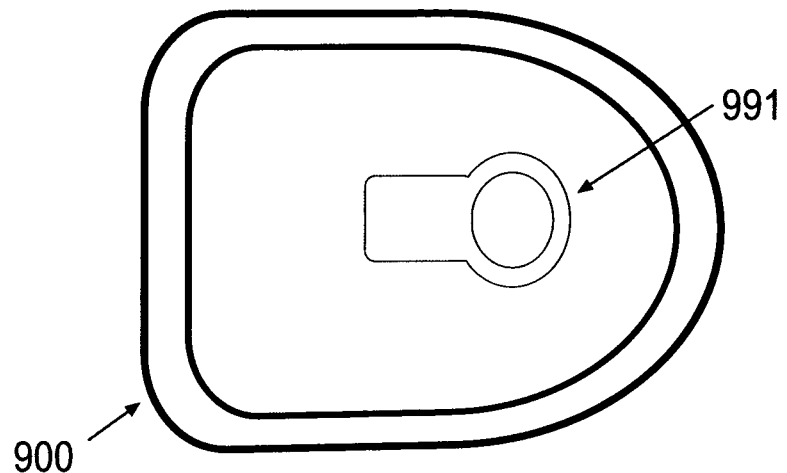

The cooling plate (991) may be configured such that a portion of it surrounds the opening at the bottom of the inserter (90), as seen in FIG. 18*c*. In some embodiments, the inserter (90) can be connected to the cradle unit (20) which has appropriate windows surrounding its well (310), as shown in FIGS. 12*c* and 13*b*. Upon attachment of the cradle unit (20) to the user's skin (5), the TEC (990) can be activated using a switch (not shown in FIG. 18*a*). Upon activation of the TEC (990), the voltage applied across the TEC (990) is converted into a temperature gradient (i.e., low temperature), thereby cooling the cooling plate (991), which in turn, cools the skin surrounding the insertion site. In some embodiments, the cooling plate (991) is in physical contact with skin (5). After a predetermined period of time, for example, no more than 5 seconds, the user can initiate the cannula insertion process. An example of this insertion process is disclosed co-owned/co-pending International Patent Application No. PCT/IL08/000860 and U.S. patent application Ser. No. 12/215,255 claiming priority to U.S. Provisional Patent Application No.60/937,214, entitled "Insertion Device for Inserting a Cannula into a Body", U.S. Provisional Patent Application No. 60/937,155, entitled "Protector for Cannula and Penetrating Member Insertable in the Body of a Patient", and U.S. Provisional Patent Application No. 60/937,163, entitled "Devices and Methods for Pain Reduction", the disclosures of which are incorporated herein by reference in their entireties. In some embodiments, the cannula release can be initiated automatically after cooling the skin around the insertion site. In some embodiments, the cooling of the skin and the release of the cannula can be pre-programmed either manually or automatically, e.g., by a designated timing mechanism (not shown) provided in the inserter (90). As can be understood by one skilled in the art, differently shaped TEC (990) can be used. In some embodiments, the TEC (990) can maintain constant contact with the skin surrounding the insertion site, while in other embodiments, the TEC (990) can be in a close proximity to the skin surrounding the insertion site so as to sufficiently cool the skin without freezing it.

FIGS. 19*a-b* show the mouse-like inserter (90) having the array of protrusions (901) surrounding its bottom opening. The protrusions can be either blunt or sharp, as shown in FIG. 10*a*. The inserter (90) connected to the cradle unit having pores surrounding its well (as shown in FIGS. 10*c* and 11*b*) can be used to relieve painful effects associated with skin piercing.

Figure 20:
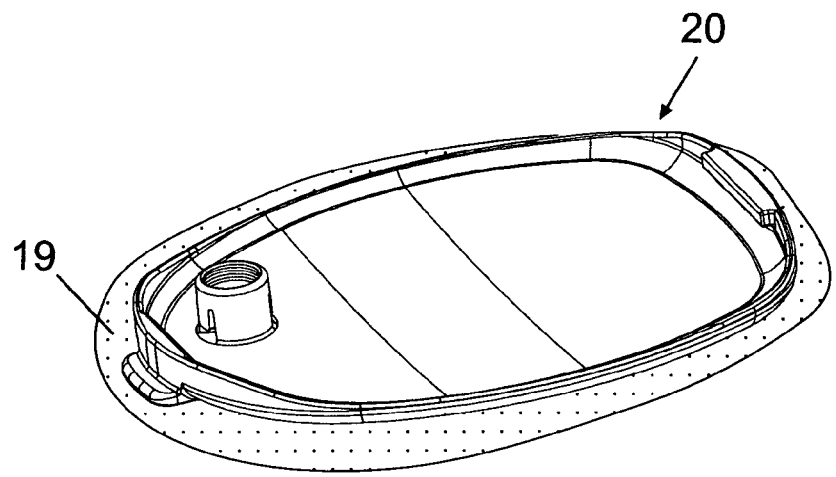
FIG. 20 shows an exemplary cradle unit provided with an anesthetic adhesive layer, according to some embodiments of the present invention.

In some embodiments, an anesthetic adhesive layer attached to the bottom of the cradle unit, or the bottom of the infusion set hub, or the bottom of the dispensing patch unit having a well assembly, can be used to relieve pain associated with cannula insertion. Such adhesive can include a predetermined percentage of an anesthetic substance, e.g., Lidocaine, Benzocaine, etc., in order to provide pain relieving effects. FIG. 20 shows the cradle unit (20) provided with an anesthetic adhesive layer (19). The anesthetic adhesive layer (19) can be configured to have the same size and shape as the cradle unit (20), or it can differently sized and/or shaped. The user attaches the cradle unit (20) to the user's skin with the layer (19) facing the skin. The anesthetic disposed on the adhesive layer (19) begins precipitating into the skin of the user, thereby providing numbing effects and reducing sensitivity of the skin. After completing this procedure the user can begin cannula insertion procedures, as discussed above.

As can be understood by one skilled in the art, the above pain reduction/alleviation/relief procedures can be used in combination with one another in order to relieve pain and stress of the user associated with cannula insertion, and specifically with skin piercing.

It will be noted that all abovementioned pain reduction means may also be implemented in inserters that enable cannula insertion at different angles, and/or that contain more than one cannula cartridge unit, as was described in co-owned/co-pending International Patent Application No. PCT/IL08/000860 and U.S. patent application Ser. No. 12/215,255 claiming priority to U.S. Provisional Patent Application No. 60/937,214, entitled "Insertion Device for Inserting a Cannula into a Body", U.S. Provisional Patent Application No. 60/937,155, entitled "Protector for Cannula and Penetrating Member Insertable in the Body of a Patient", and U.S. Provisional Patent Application No. 60/937,163, entitled "Devices and Methods for Pain Reduction", all filed Jun. 25, 2007, the disclosures of which are incorporated herein by reference in their entireties. Furthermore, all above-mentioned pain reduction means may also be implemented in protectors that can accommodate differently sized/shaped cannulae and/or that contain more than one penetrating cartridge, as disclosed in co-owned/co-pending U.S. patent application Ser. No.12/215,219 and International Patent Application No. PCT/IL08/0000859 claiming priority to U.S. Provisional Patent Application No. 60/937,155, entitled "Protector for Cannula and Penetrating Member Insertable in the Body of a Patient", U.S. Provisional Patent Application No. 60/937,214, entitled "Insertion Device for Inserting a Cannula into a Body", and U.S. Provisional Patent Application No. 60/937,163, entitled "Devices and Methods for Pain Reduction", the disclosures of which are incorporated herein by reference in their entireties.

In some embodiments, the insertion device can be an inserter or a protector discussed above with regard to FIGS. 1a-20 and can accommodate insertion of a subcutaneously insertable element that can include a cannula, a probe, and/or a sensor. The subcutaneously insertable element can be used for both fluid delivery and analyte sensing as well as other tasks.

While the invention has been described with reference to above embodiments and examples, those skilled in the art recognize that various modifications may be made to the invention without departing from the spirit and scope thereof.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The applicant reserves the right to pursue such inventions in later claims.

What is claimed:

1. A system for delivery of a therapeutic fluid to a body of a patient and/or for sensing of a bodily analyte comprising:
   a device suitable for at least one of delivery of the therapeutic fluid and sensing of the bodily analyte, the device including a skin adherable portion having a first opening;
   a subcutaneously insertable element and a penetrating member configured to be protracted through the opening to penetrate a skin of the patient; and
   an insertion apparatus removably coupleable to the skin adherable portion of the device, the insertion apparatus comprising:
      a housing adapted for accommodating therein at least one penetrating cartridge which includes the subcutaneously insertable element and the penetrating member;
      a displacement mechanism configured to protract the penetrating cartridge towards the body of the patient; wherein protraction of the penetrating cartridge results in penetration of the skin by the penetrating member and insertion of at least the subcutaneously insertable element into the body of the patient; and
   at least one pain reduction mechanism for alleviating pain associated with the penetrating of the skin by the subcutaneously insertable element and the penetrating member, the at least one pain reduction mechanism comprising:
      a first portion provided by the insertion apparatus; and
      receiving means provided by the skin adherable portion for receiving the first portion and allowing the first portion to protrude through the skin adherable portion when the insertion apparatus is coupled to the skin adherable portion.

2. The system according to claim 1, wherein the skin adherable portion of the device is selected from a group consisting of: a dispensing unit, a sensing device, a cradle unit, and a hub of an infusion set.

3. The system according to claim 1, wherein the first portion of the at least one pain reduction mechanism is disposed at a bottom portion of the housing, wherein the bottom portion is configured to face the skin of the patient.

4. The system according to claim 3, wherein the at least one pain reduction mechanism is detachably connected to the bottom portion of the housing.

5. The system according to claim 3, wherein the first potion of the at least one pain reduction mechanism comprises a plurality of protrusions; and
   wherein the receiving means of the at least one pain reduction mechanism comprises a plurality of second openings adjacent the first opening, the second openings being configured and arranged to correspond to the plurality of protrusions such that upon coupling the insertion apparatus to the skin adherable portion of the device, the plurality of protrusions protrude through the plurality of corresponding second openings.

6. The system according to claim 5, wherein at least some of the plurality of protrusions include a sharp end.

7. The system according to claim 5, wherein at least some of the plurality of protrusions include a blunt end.

8. The system according to claim 5, wherein each of the plurality of protrusions has a length in a range of about 1 mm to about 5 mm and a diameter in a range of about 50 µm to about 2000 µm.

9. The system according to claim 3, wherein the first portion of the at least one pain reduction mechanism comprises one or more cooling plates; and
   wherein the receiving means of the at least one pain reduction mechanism comprises one or more windows corresponding to the cooling plates of the first portion such that upon coupling the insertion apparatus to the skin adherable portion of the device, the one or more cooling plates fit within the one or more corresponding windows.

10. The system according to claim 1, wherein the at least one pain reduction mechanism comprises a thermoelectric cooler such that the first portion of the at least one pain reduction mechanism comprises at least one cooling plate disposed at a bottom portion of the housing of the insertion apparatus, wherein the bottom portion is configured to face the skin of the patient; and
   wherein the temperature of the at least one cooling plate is lowered upon application of voltage to the thermoelectric cooler.

11. The system according to claim 10, wherein the receiving means of the at least one pain reduction mechanism includes at least one window corresponding to the at least one cooling plate such that upon coupling the insertion apparatus to the skin adherable portion of the device, the at least one cooling plate is accommodated by the at least one corresponding window.

12. The system according to claim 1, wherein the at least one pain reduction mechanism includes a container having a cooling substance releasable towards the skin of the patient.

13. The system according to claim 12, wherein the cooling substance container includes an outlet port and is coupled to an actuation mechanism;
wherein upon actuation of the actuation mechanism the cooling substance is released from the container via the outlet port.

14. The system according to claim 1, wherein the insertion apparatus further comprises a protective member accommodating therein the at least one penetrating cartridge, wherein the protective member is adapted for loading into the housing.

15. The system according to claim 1, wherein the displacement mechanism comprises a rod for manually pushing the penetrating cartridge toward the body of the patient.

16. The system according to claim 1, wherein the displacement mechanism includes a loadable spring for forcible displacement of the penetrating cartridge toward the body of the patient.

17. The system according to claim 1, wherein the displacement mechanism is further configured to retract the penetrating member subsequently to the insertion of the subcutaneously insertable element.

18. The system according to claim 1, wherein the receiving means is configured to provide a secure connection between the skin adherable portion and the insertion apparatus.

19. The system according to claim 1, wherein the receiving means comprises bridges, and the first portion of the at least one pain reduction mechanism comprises grooves configured to fit over the grooves of the receiving means when the insertion apparatus is coupled to the skin adherable portion.

20. The system according to claim 1, wherein the insertion apparatus does not fully protrude through the skin adherable portion of the device.

21. A system for delivery of a therapeutic fluid to a body of a patient and/or for sensing of a bodily analyte comprising:
a skin-adherable device suitable for at least one of delivery of the therapeutic fluid and sensing of the bodily analyte, the device defining a first opening;
a subcutaneously insertable element and a penetrating member configured to be protracted through the opening to penetrate a skin of the patient;
an insertion apparatus removably coupleable to the skin adherable device, the insertion apparatus comprising:
a housing adapted for accommodating therein at least one penetrating cartridge which includes the subcutaneously insertable element and the penetrating member;
a displacement mechanism configured to protract the penetrating cartridge towards the body of the patient, and insert the penetrating member and the subcutaneously insertable element through the skin and into the body of the patient; and
a first pain reduction means for alleviating pain associated with the penetrating of the skin by the subcutaneously insertable element and the penetrating member;
wherein the skin-adherable device further comprises receiving means for receiving the first pain reduction means and allowing the first pain reduction means to protrude through the skin adherable device when the insertion apparatus is coupled to the skin adherable device; the receiving means being arranged adjacent to the first opening.

22. The system according to claim 21, wherein the receiving means comprises a plurality of second openings surrounding the first opening.

23. The system according to claim 21, wherein the skin-adherable device further comprises a second pain reduction means for alleviating pain associated with the penetrating of the skin by the subcutaneously insertable element and the penetrating member.

24. The system according to claim 23, wherein the second pain reduction means comprises one or more cooling plates.

25. A system for delivery of a therapeutic fluid to a body of a patient and/or for sensing of a bodily analyte comprising:
a skin-adherable device suitable for at least one of delivery of the therapeutic fluid and sensing of the bodily analyte, the device defining a first openings;
a subcutaneously insertable element and a penetrating member configured to be protracted through the opening to penetrate a skin of the patient;
an insertion apparatus removably coupleable to the skin adherable device, the insertion apparatus comprising:
a protective member accommodating therein a penetrating cartridge which includes the subcutaneously insertable element and the penetrating member; the protective member comprising a first pain reduction means for alleviating pain associated with the penetrating of the skin by the subcutaneously insertable element and the penetrating member;
a housing adapted for accommodating therein the protective member;
a displacement mechanism configured to protract the penetrating cartridge towards the body of the patient, and insert the penetrating member and the subcutaneously insertable element through the skin and into the body of the patient; and
wherein the skin-adherable device further comprises receiving means for receiving the first pain reduction means and allowing the first pain reduction means to protrude through the skin adherable device when the insertion apparatus is coupled to the skin adherable device; the receiving means being arranged adjacent to the first opening.

26. The system according to claim 21, wherein the first pain reduction means comprises a plurality of protrusions disposed at a bottom portion of the protective member.

27. The system according to claim 21, wherein the receiving means comprises a plurality of second openings surrounding the first opening.

28. A system for delivery of a therapeutic fluid to a body of a patient and/or for sensing of a bodily analyte comprising:
a device suitable for at least one of delivery of the therapeutic fluid and sensing of the bodily analyte, the device including a skin adherable portion having a first opening through which a subcutaneously insertable element and a penetrating member are capable of being protracted to penetrate a skin of the patient;
an insertion apparatus removably coupleable to the skin adherable portion of the device, the insertion apparatus comprising:
a housing adapted for accommodating therein at least one penetrating cartridge including the subcutaneously insertable element and the penetrating member;
a displacement mechanism configured to protract the penetrating cartridge towards the body of the patient;

wherein protraction of the penetrating cartridge results in penetration of the skin by the penetrating member and insertion of at least the subcutaneously insertable element into the body of the patient; and at least one pain reduction mechanism for alleviating pain associated with the penetrating of the skin by the subcutaneously insertable element and the penetrating member, the at least one pain reduction mechanism comprising:

a first portion provided by the insertion apparatus; and receiving means provided by the skin adherable portion which is configured to receive the first portion and allow the first portion to protrude through the skin adherable portion without penetrating the skin of the patient when the insertion apparatus is coupled to the skin adherable portion.

29. The system according to claim 28, wherein the first portion protruding through the receiving means without penetrating the skin of the patient comprises the first portion protruding through the skin adherable portion to apply pressure to the skin adjacent the opening.

\* \* \* \* \*

UNITED STATES PATENT AND TRADEMARK OFFICE
CERTIFICATE OF CORRECTION

PATENT NO.       : 8,715,232 B2                                   Page 1 of 1
APPLICATION NO. : 12/452187
DATED            : May 6, 2014
INVENTOR(S)      : Yodfat et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 70 days.

Signed and Sealed this

Twenty-ninth Day of September, 2015

Michelle K. Lee
*Director of the United States Patent and Trademark Office*